(12) United States Patent
Karidis et al.

(10) Patent No.: US 7,355,855 B2
(45) Date of Patent: Apr. 8, 2008

(54) COMPLIANT THERMAL INTERFACE STRUCTURE UTILIZING SPRING ELEMENTS

(75) Inventors: John P. Karidis, Ossining, NY (US); Mark D. Schultz, Ossining, NY (US); Bucknell C. Webb, Ossining, NY (US)

(73) Assignee: International Business Machines Corporation, Armonk, NY (US)

( * ) Notice: Subject to any disclaimer, the term of this patent is extended or adjusted under 35 U.S.C. 154(b) by 192 days.

(21) Appl. No.: 11/151,830

(22) Filed: Jun. 14, 2005

(65) Prior Publication Data

US 2006/0279935 A1   Dec. 14, 2006

(51) Int. Cl.
  *H05K 7/20* (2006.01)
(52) U.S. Cl. ...................... 361/710; 361/704
(58) Field of Classification Search ................ 361/710, 361/698, 699, 711
See application file for complete search history.

(56) References Cited

U.S. PATENT DOCUMENTS

| | | | |
|---|---|---|---|
| 5,528,456 A * | 6/1996 | Takahashi | 361/704 |
| 5,548,090 A * | 8/1996 | Harris | 174/252 |
| 6,259,602 B1 * | 7/2001 | Malhammar | 361/704 |
| 6,317,326 B1 * | 11/2001 | Vogel et al. | 361/704 |
| 6,411,513 B1 * | 6/2002 | Bedard | 361/704 |
| 6,528,878 B1 * | 3/2003 | Daikoku et al. | 257/714 |
| 6,894,908 B1 * | 5/2005 | Clark et al. | 361/825 |
| 6,898,082 B2 * | 5/2005 | Dessiatoun et al. | 361/699 |
| 6,903,929 B2 * | 6/2005 | Prasher et al. | 361/699 |
| 7,019,395 B2 * | 3/2006 | Hirano et al. | 257/717 |
| 7,019,971 B2 * | 3/2006 | Houle et al. | 361/699 |
| 7,028,761 B2 * | 4/2006 | Lee et al. | 165/104.33 |
| 2006/0278371 A1 * | 12/2006 | Karidis et al. | 165/104.33 |
| 2006/0279932 A1 * | 12/2006 | Karidis et al. | 361/704 |

* cited by examiner

*Primary Examiner*—Hae Moon Hyeon
(74) *Attorney, Agent, or Firm*—Michael J. Buchenhorner; Vazken Alexanian

(57) ABSTRACT

A structure for cooling an electronic device is disclosed. The structure includes a top layer disposed over the electronic device. The structure further includes a plurality of spring elements disposed between the top layer and the electronic device for providing a heat path from the electronic device and wherein the plurality of spring elements provide mechanical compliance. In one alternative, the structure further includes a solid heat-conducting layer disposed over the electronic device, wherein the plurality of spring elements are coupled to the solid heat-conducting layer.

19 Claims, 24 Drawing Sheets

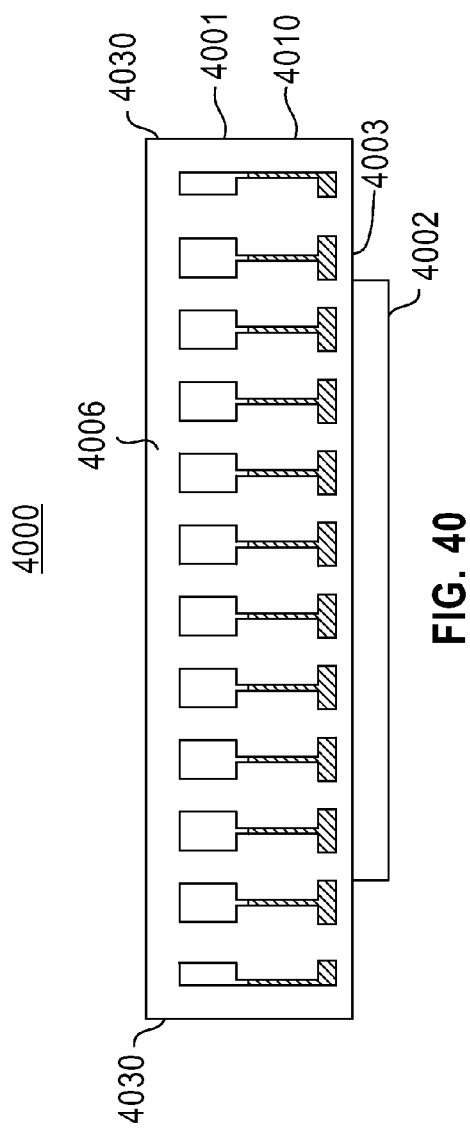
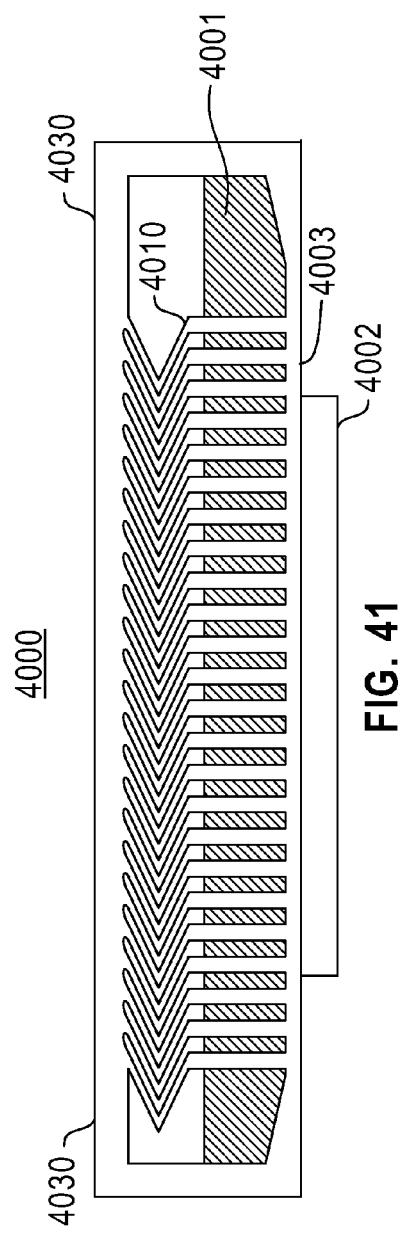

COMPLIANT THERMAL INTERFACE STRUCTURE UTILIZING SPRING ELEMENTS

CROSS-REFERENCE TO RELATED APPLICATIONS

Not Applicable.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

FIELD OF THE INVENTION

The invention disclosed broadly relates to the field of cooling devices for electronic components, and more particularly relates to the field of heat sinks for microprocessors.

BACKGROUND OF THE INVENTION

During the normal operation of a computer, integrated circuit devices generate significant amounts of heat. This heat must be continuously removed, or the integrated circuit device may overheat, resulting in damage to the device and/or a reduction in operating performance. Cooling devices, such as heat sinks, have been used in conjunction with integrated circuit devices in order to avoid such overheating. Generally, a passive heat sink in combination with a system fan has provided a relatively cost-effective cooling solution. In recent years, however, the power of integrated circuit devices such as microprocessors has increased exponentially, resulting in a significant increase in the amount of heat generated by these devices, thereby necessitating a more efficient cooling solution.

It is becoming extremely difficult to extract the heat generated by semiconductor devices (processors, in particular) that continue to generate more and more heat in the same amount of space. Heat is typically extracted by coupling a heat spreader and thermal cap to the semiconductor and a heat sink. This coupling typically involves a thermal paste which serves to not only transfer heat but provide some degree of mechanical compliance to compensate for dimensional changes driven by the high temperatures. This paste is often a weak link in the thermal path. Attempts to thin this layer have resulted in failure of the layer when it is exposed to dimensional changes due to heat.

One approach to this problem involves a spring loaded assembly of fingers with thermal paste in between them and a thermal paste interface to the chip. This solution is limited in performance by the thermal paste and in design by the requirement for consistent spring loading. Liquid metal has been proposed on its own as a thermal interface material, but could have significant difficulty dealing with large z-axis thermally induced excursions, requiring some compliance elsewhere in the package or (if the largest spacing seen is still thermally acceptable) some sort of edge reservoir design.

Therefore, a need exists to overcome the problems with the prior art as discussed above, and particularly for a way to cool small electronic devices using a thermally compliant material.

SUMMARY OF THE INVENTION

Briefly, according to an embodiment of the present invention, a structure for cooling an electronic device includes a top layer disposed over the electronic device. The structure further includes a plurality of spring elements disposed between the top layer and the electronic device for providing a heat path from the electronic device and wherein the plurality of spring elements provide mechanical compliance. In another embodiment of the present invention, the structure further includes a solid heat-conducting layer disposed over the electronic device, wherein the plurality of spring elements are coupled to the solid heat-conducting layer.

According to another embodiment of the present invention, the structure for cooling an electronic device includes a rigid top layer disposed over the electronic device. The structure further includes a plurality of spring elements disposed between the top layer and the electronic device for providing a heat path from the electronic device and wherein the plurality of spring elements provide mechanical compliance. The structure further includes any one of a liquid and semi-solid thermal interface material disposed between the plurality of spring elements. In another embodiment of the present invention, the structure further includes a solid heat-conducting layer disposed over the electronic device, wherein the plurality of spring elements are coupled to the solid heat-conducting layer.

The terms "above" and "below" are only used herein to relative positions of the components and do not imply any orientation of the components.

BRIEF DESCRIPTION OF THE DRAWINGS

The subject matter, which is regarded as the invention, is particularly pointed out and distinctly claimed in the claims at the conclusion of the specification. The foregoing and other features and also the advantages of the invention will be apparent from the following detailed description taken in conjunction with the accompanying drawings. Additionally, the left-most digit of a reference number identifies the drawing in which the reference number first appears.

FIG. 40 is a cross-sectional side view of a cooling structure for a reduced-size electronic device, the cooling structure includes a container for containing a liquid with vaporizing capability, a compliant membrane and spring elements with fins, according to one embodiment of the present invention.

FIG. 41 is another cross-sectional side view of the cooling structure of FIG. 40.

DETAILED DESCRIPTION

Figure 1:
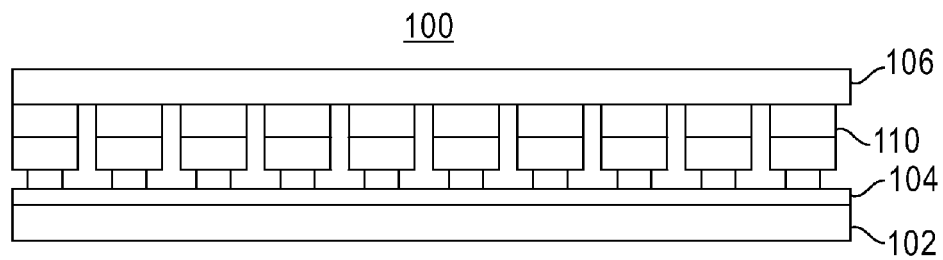
FIG. 1 is a cross-sectional side view of a cooling structure for an electronic device, the cooling structure including spring elements and a plate, according to one embodiment of the present invention.

The present invention includes an array of high thermal conductivity spring elements (made of copper, for example) with a high packing density, wherein the spring elements are attached to or integrated with a thermally conductive plate having either a flexible or somewhat rigid top (such as a heat sink or cold cap side). In another embodiment of the present invention, the array of spring elements can be either coupled or placed in contact with (directly or via an interface material) a subject electronic device, such as a semiconductor device.

In another embodiment of the present invention, the array of spring elements can be coupled to or integrated with a conformable high thermal conductivity bottom membrane. When coupled with a membrane, the array of spring elements can have a relatively small contact area that rapidly increases in cross section to the full cross section of the spring element. This arrangement prevents the end of the spring elements from adding unwanted rigidity to the conformable membrane with minimal thermal resistance. Similarly, the narrowing cross-section feature can also be implemented in the case where the array of spring elements are either coupled or placed in contact with a subject electronic device. However, if a very thin thermal interface material is present between the array of spring elements and the electronic device and there is high spatial frequency content in the lack of flatness of the electronic device surface, it may be desirable to narrow the spring element ends.

In another embodiment of the present invention, if pure perpendicular motion is desirable upon compression in the case where the array of spring elements are coupled to or integrated with a conformable high thermo conductivity bottom membrane, the array of spring elements may have narrow sections at the ends where they contact a heat sink. Packing density can be as high as practical without interference within an expected compliance range. In another embodiment of the present invention, the array of spring elements can be a particular thickness through their entire length.

In another embodiment of the present invention, if the space occupied by the array of spring elements can be sealed without compromising compliance, a thermally conductive liquid (such as liquid metal) can be added to reduce the thermal path length. In this embodiment, the present invention takes advantage of useful thermal and physical characteristics of liquid metal. Liquid metal is used as a thermal interface material between the array of spring elements and a microprocessor or a plate coupled thereto.

The present invention is advantageous as it provides compliance in a location other than (or in addition to) the gap area between the microprocessor and the heat conducting portion of the invention neighboring the microprocessor. The present invention is further advantageous as the forces on the microprocessor exerted by physical changes brought on by heat in the x, y and z directions do not vary greatly. Further, the present invention allows for z-compliance by utilizing the array of spring elements. Thus, the present invention eliminates the necessity for compliance in a film disposed between the microprocessor and a heat spreader or heat sink. Additionally, the present invention does not require the use of high-viscosity thermal paste, which is not effective in very thin layers.

FIG. 1 is a cross-sectional side view of a cooling structure for an electronic device, the cooling structure including spring elements and a plate, according to one embodiment of the present invention. FIG. 1 shows a heat-producing electronic device, a microprocessor 102, located along the bottom of the assembly 100. Disposed on the microprocessor 102 is a first layer 104, which can be a solid layer for providing a heat path from the microprocessor 102 to the upper elements of the assembly 100. Examples of a solid heat-conducting layer used for this purpose are a thermally conductive adhesive and a solder such as indium. The first layer 104 is a planar surface that rests in contact with the microprocessor 102. In another embodiment of the present invention, the first layer 104 can be a conformable high thermal conductivity membrane such as a copper sheet. In an embodiment where the first layer 104 is a membrane, an additional layer of high thermal conductivity material would be disposed between the microprocessor 102 and the membrane.

The cooling structure assembly 100 further includes an array of spring elements 110 that are in contact with or are coupled with the first layer 104. The array of spring elements 110 includes a plurality of springs extending in the upper direction away from the source of the heat, the microprocessor 102. Each of the spring elements 110 draw heat away from the microprocessor 102 and allows the heat to radiate out from the increased surface area of the spring elements 110. Each of the spring elements 110 is formed of a heat conducting material such as copper. Further, each of the array of spring elements 110 exhibits qualities of a spring, which allows for compression and elongation in the z-direction, i.e., the up and down direction, and in the x, y-directions, i.e., the sideways directions. This provides heat compliance in accordance with dimensional changes in the microprocessor 102 during use.

Each of the array of spring elements 110 comprises a spring such as a leaf spring or a helix spring for offering resistance when loaded. Each of the array of spring elements 110 provide compliance between the top layer 106 and the microprocessor 102 and works to keep the top layer 106 in close proximity to the microprocessor 102. The composition and shape of each of the array of spring elements 110 is described in greater detail below.

The cooling structure assembly 100 further includes a top layer 106 comprising a planar surface, wherein the array of spring elements 110 contact the top layer 106. The top layer 106 can be a solid layer for providing a heat path from the microprocessor 102 to the upper elements of the assembly 100. The top layer 106 can be a solid heat-conducting layer such as a thermally conductive adhesive, solder, or solid metal structure.

Figure 2:
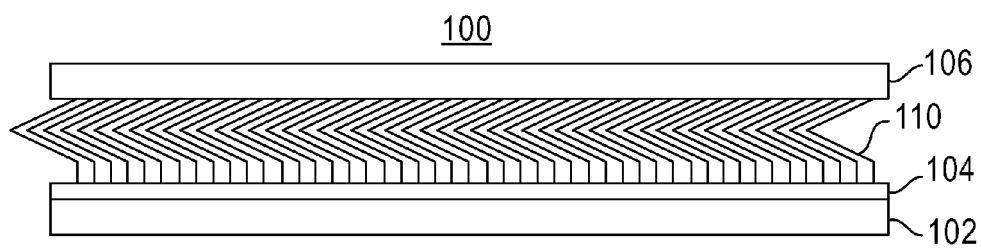
FIG. 2 is another cross-sectional side view of the cooling structure of FIG. 1.

FIG. 2 is another cross-sectional side view of the cooling structure of FIG. 1. FIG. 2 shows the cooling structure assembly 100 comprising the top layer 106, the first layer 104 and the array of spring elements 110 disposed between them. FIG. 2 also shows the microprocessor 102 at the bottom of the cooling structure assembly 100.

Figure 3:
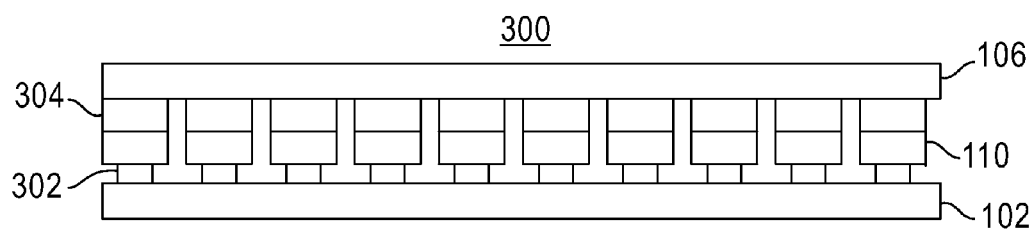
FIG. 3 is a cross-sectional side view of a cooling structure for an electronic device, the cooling structure including spring elements, according to one embodiment of the present invention.

FIG. 3 is a cross-sectional side view of a cooling structure for an electronic device, the cooling structure including spring elements, according to one embodiment of the present invention. FIG. 3 shows the cooling structure assembly 300 comprising the top layer 106, the microprocessor 102 at the bottom of the cooling structure assembly 300 and the array of spring elements 110 disposed between them. The cooling structure assembly 300 of FIG. 3 is similar to the cooling structure assembly 100 of FIG. 1 except for the presence of the first layer 104.

In this embodiment of the present invention, the array of spring elements 110 are either coupled or placed in contact with (directly or within an interface material) the microprocessor 102. In another embodiment, the array of spring elements 110 can have a relatively small profile at the end 302 of the spring elements that contact the microprocessor 102. The profile would rapidly increase in size to the full cross section of the spring element at the end 304 of the spring elements that contact the top layer 106. This arrangement prevents the end 302 of the array of spring elements 110 from adding unwanted rigidity to the microprocessor 102 without any substantial thermal resistance. In another embodiment, if a very thin thermal interface material is present between the array of spring elements 110 and the microprocessor 102 and there is high spatial frequency content in the lack of flatness of the surface of the microprocessor 102, it may be desirable to narrow the spring element ends. In another embodiment of the present invention, the array of spring elements 110 can be a particular thickness through their entire length.

Figure 4:
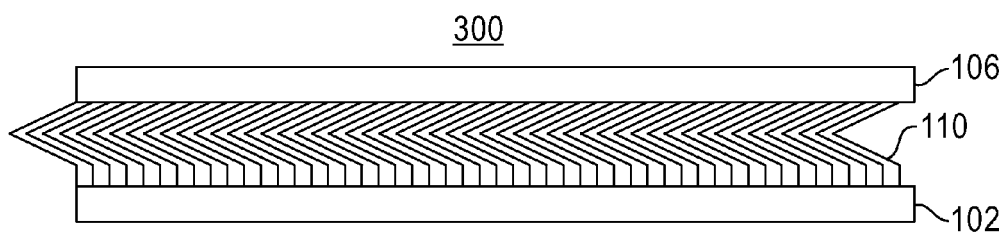
FIG. 4 is another cross-sectional side view of the cooling structure of FIG. 3.

FIG. 4 is another cross-sectional side view of the cooling structure of FIG. 3. FIG. 4 shows the cooling structure assembly 300 comprising the top layer 106, the microprocessor 102 at the bottom of the cooling structure assembly 300 and the array of spring elements 110 disposed between them.

Figure 5:
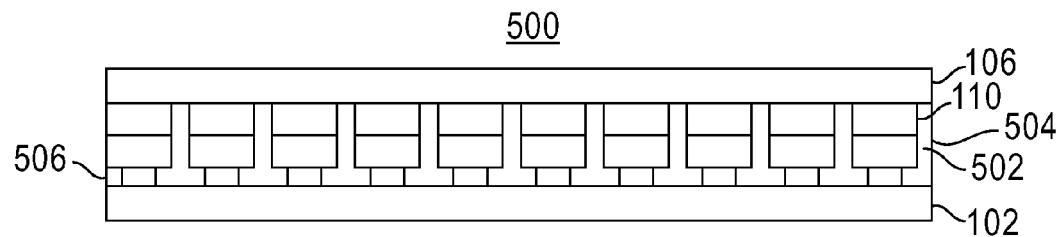
FIG. 5 is a cross-sectional side view of a cooling structure for an electronic device, the cooling structure including spring elements and a liquid, according to one embodiment of the present invention.

FIG. 5 is a cross-sectional side view of a cooling structure for an electronic device, the cooling structure including spring elements and a liquid, according to one embodiment of the present invention. FIG. 5 shows the cooling structure assembly 500 comprising a top layer 106, a microprocessor 102 at the bottom of the cooling structure assembly 500 and an array of spring elements 110 disposed between them. Also included is a thermal interface material 502 and a seal 504 for containing the thermal interface material 502. The cooling structure assembly 500 of FIG. 5 is similar to the cooling structure assembly 300 of FIG. 3 except for the presence of the thermal interface material 502 and the seal 504. In this embodiment of the present invention, the array of spring elements 110 are either coupled or placed in contact with (directly or within an interface material) the microprocessor 102.

The thermal interface material 502 can be a liquid material or a non-rigid solid material. In one embodiment, the thermal interface material 502 is a non-metal liquid, such as oil or water, or a liquid metal such as mercury, gallium or a gallium alloy such as with tin or indium. A liquid 502 can be sealed with a seal 504 or container so as to restrict the escape of the liquid from the desired area over the microprocessor 102. The liquid nature of the liquid 502 allows the substance to fill the areas created by the gap created between each of the spring elements 110. The liquid 502 provides a heat path from the microprocessor 102 to the upper elements of the assembly 500 as the heat travels from the microprocessor 102 to the top layer 106.

Figure 6:
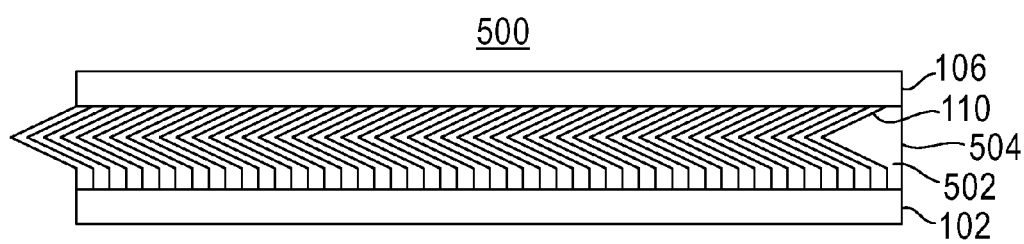
FIG. 6 is another cross-sectional side view of the cooling structure of FIG. 5.

FIG. 6 is another cross-sectional side view of the cooling structure of FIG. 5. FIG. 6 shows the cooling structure assembly 500 comprising a top layer 106, a microprocessor 102 at the bottom of the cooling structure assembly 500 and an array of spring elements 110 disposed between them. Also included is a thermal interface material 502 and a seal 504 for containing the thermal interface material 502.

Figure 7:
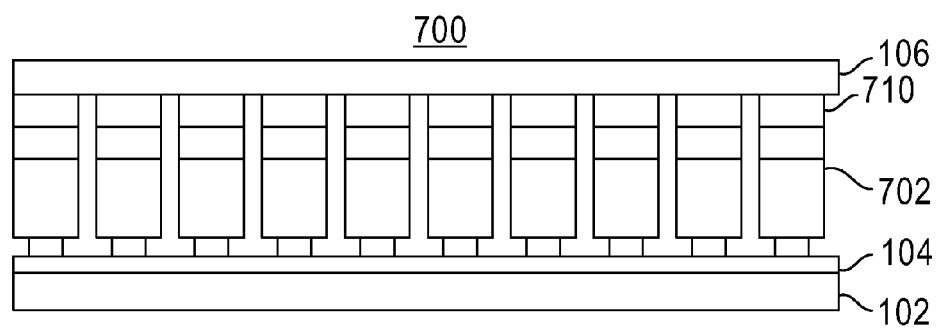
FIG. 7 is a cross-sectional side view of a cooling structure for an electronic device, the cooling structure including spring elements with fins and a plate, according to one embodiment of the present invention.

FIG. 7 is a cross-sectional side view of a cooling structure for an electronic device, the cooling structure including spring elements with fins and a plate, according to one embodiment of the present invention. FIG. 7 shows the cooling structure assembly 700 comprising the top layer 106, the first layer 104 and the array of spring elements 710 disposed between them. FIG. 7 also shows the microprocessor 102 at the bottom of the cooling structure assembly 700. In another embodiment of the present invention, the first layer 104 can be a conformable high thermal conductivity membrane such as a copper sheet. In an embodiment where the first layer 104 is a membrane, an additional layer of high thermal conductivity material would be disposed between the microprocessor 102 and the membrane. The cooling structure assembly 700 of FIG. 7 is similar to the cooling structure assembly 100 of FIG. 1 except for the presence of the elongated fin portion 702 of each of the array of spring elements 710.

In another embodiment of the present invention, a coolant would flow between and among the array of spring elements 710. The coolant can be a liquid material or a gas material. In one embodiment, the coolant is a non-metal liquid, such as oil or water, or a liquid metal such as mercury, gallium or a gallium alloy such as with tin or indium. The liquid nature of the liquid allows the substance to fill the areas created by the gap created between each of the spring elements 710. The liquid provides a heat path from the microprocessor 102 to the upper elements of the assembly 700 as the heat travels from the microprocessor 102 to the top layer 106.

The portion 702 of each of the array of spring elements 710 comprises a plurality of fins extending in the upper direction away from the source of the heat, the microprocessor 102. The inclusion of the fins serves to effectively increase the surface area of the surface of the first layer 104, which serves to dissipate heat into a cooling gas or liquid. Each fin draws heat away from the microprocessor 102 and allows the heat to be conducted out from the increased surface area of the fins. The first layer 104 is a planar surface that rests in contact with the microprocessor 102.

Figure 8:
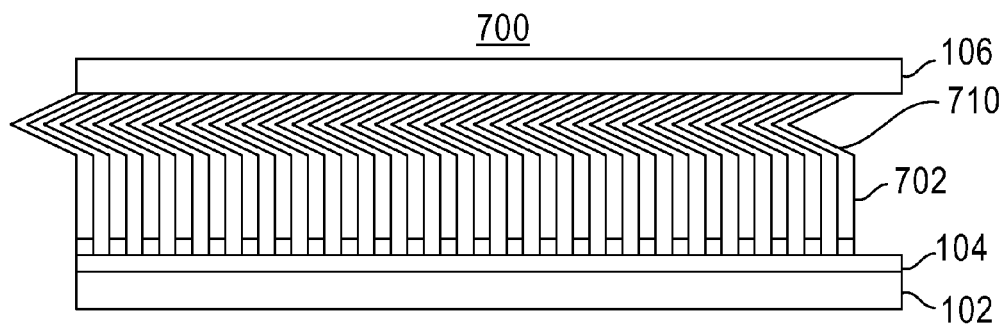
FIG. 8 is another cross-sectional side view of the cooling structure of FIG. 7.

FIG. 8 is another cross-sectional side view of the cooling structure of FIG. 7. FIG. 8 shows the cooling structure assembly 700 comprising the top layer 106, the first layer 104 and the array of spring elements 710 disposed between them. FIG. 8 also shows the microprocessor 102 at the bottom of the cooling structure assembly 700.

Figure 9:
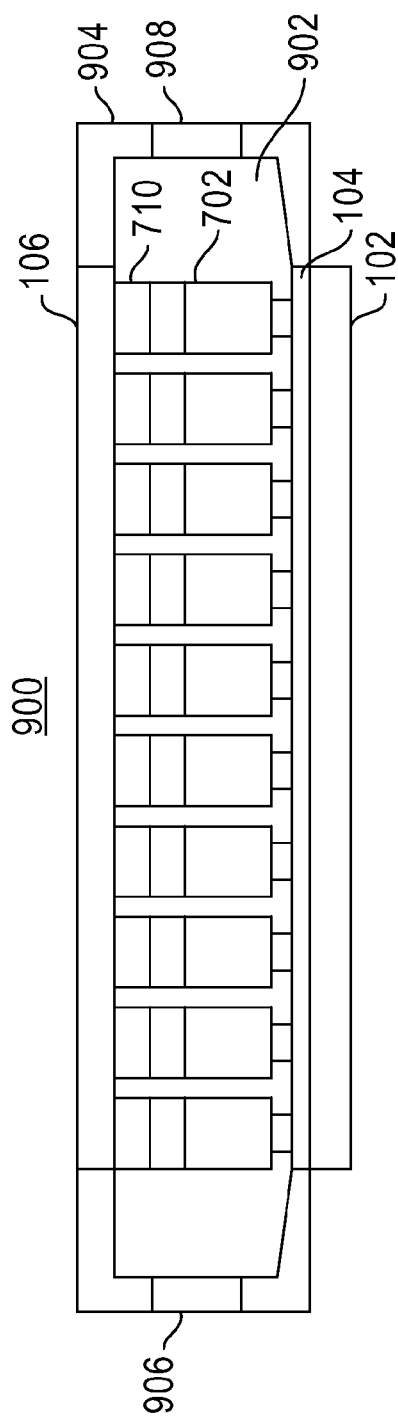
FIG. 9 is a cross-sectional side view of a cooling structure for an electronic device, the cooling structure including spring elements with a fin, a plate and a liquid, according to one embodiment of the present invention.

FIG. 9 is a cross-sectional side view of a cooling structure for an electronic device, the cooling structure including spring elements with a fin, a plate and a liquid, according to one embodiment of the present invention. FIG. 9 shows the cooling structure assembly 900 comprising the top layer 106, the first layer 104 and the array of spring elements 710 disposed between them. FIG. 9 also shows the microprocessor 102 at the bottom of the cooling structure assembly 900, a cooling gas or liquid 902 (i.e., coolant), a seal 904 and a cooling gas or liquid inlet/outlet pair 906 and 908. The cooling structure assembly 900 of FIG. 9 is similar to the cooling structure assembly 700 of FIG. 7 except for the provisions for handling a coolant 902, such as seal 904 and inlet/outlet pair 906 and 908. The cooling structure 900 can also include a pair of flow-restricting end-plates (not shown in this figure but described in greater detail below).

The coolant 902 can be a gas, a non-metal liquid material, such as oil or water, or a metal liquid material such as mercury, gallium or a gallium alloy such as with tin or indium. The coolant 902 is described in greater detail with reference to FIG. 7 above.

FIG. 9 also shows an inlet/outlet pair 906 and 908 for allowing ingress and egress of the coolant 902. The inlet 906 allows for the intake of the coolant 902 as it is pumped or otherwise pushed or propelled into the assembly 900. As the coolant 902 travels in the space filling the areas created by the gap created between the microprocessor 102 and the top layer 106, the coolant 902 absorbs the heat emanated from the first layer 104 and the array of spring elements 710, including the fin structure 702. The outlet 908 allows for the egress of the coolant 902 as it is pumped or otherwise pulled or propelled out of the assembly 900 for cooling and eventual recycling into the assembly 900.

Figure 10:
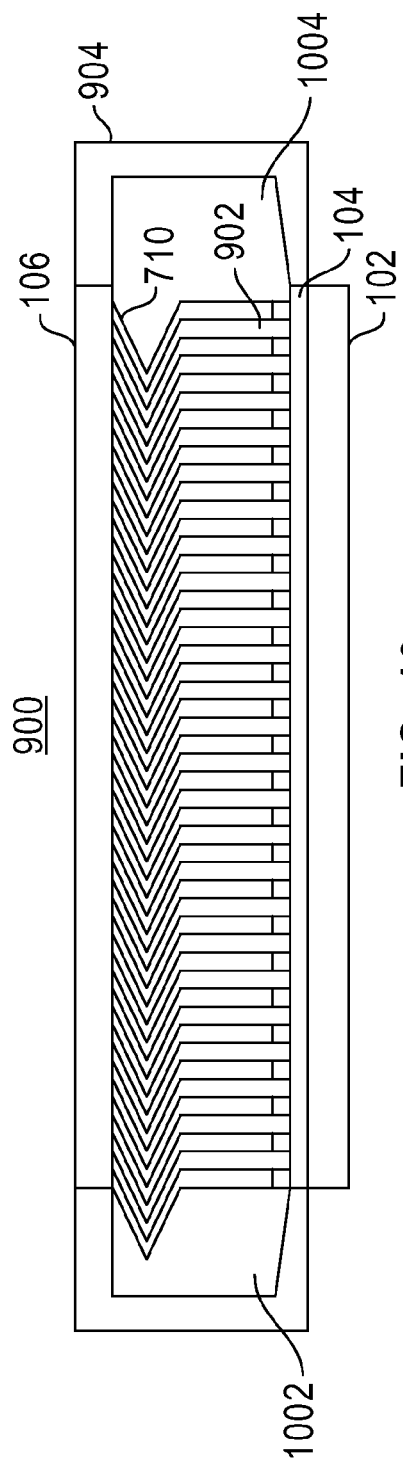
FIG. 10 is another cross-sectional side view of the cooling structure of FIG. 9.

FIG. 10 is another cross-sectional side view of the cooling structure of FIG. 9. FIG. 10 shows the cooling structure assembly 900 comprising the top layer 106, the first layer 104 and the array of spring elements 710 disposed between them. FIG. 10 also shows the microprocessor 102 at the bottom of the cooling structure assembly 900, a coolant 902 and a seal 904. The cooling structure 900 can also include a pair of flow-restricting end-plates 1002 and 1004 that fill the area on either end of the array of spring elements 710 in FIG. 10. The purpose of the end-plates 1002 and 1004 is to restrict the flow of the coolant 902 into those spaces so as to force the coolant 902 to flow in the area between the multiple spring elements, which is where a higher degree of heat dissipation occurs.

Figure 11:
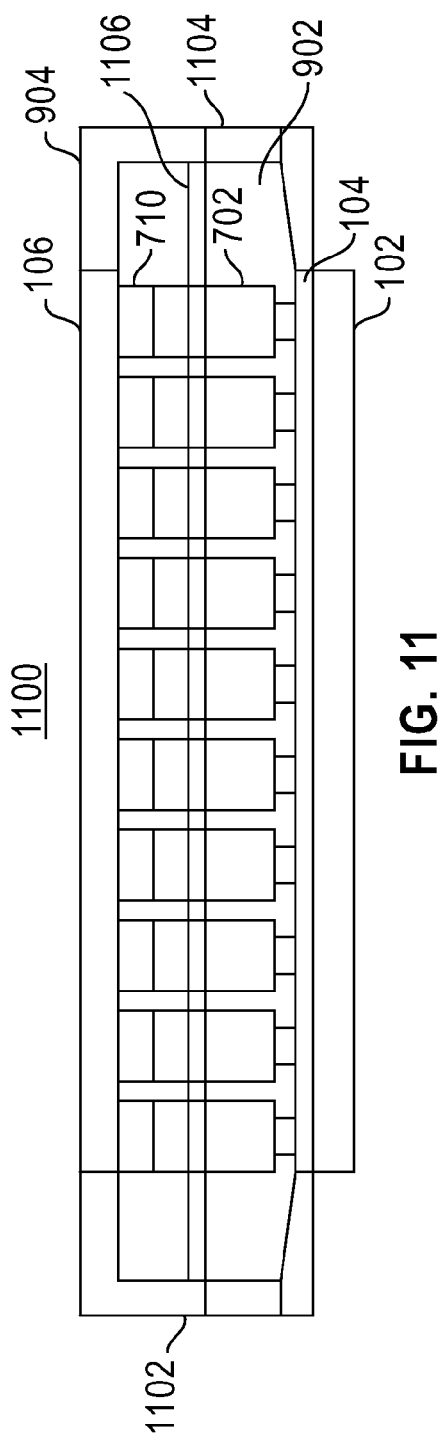
FIG. 11 is a cross-sectional side view of a cooling structure for an electronic device, the cooling structure including spring elements with a fin, a plate, a seal and a liquid, according to one embodiment of the present invention.

FIG. 11 is a cross-sectional side view of a cooling structure for an electronic device, the cooling structure including spring elements with a fin, a plate, a seal and a liquid, according to one embodiment of the present invention. FIG. 11 shows the cooling structure assembly 1100 comprising the top layer 106, the first layer 104 and the array of spring elements 710 disposed between them. FIG. 11 also shows the microprocessor 102 at the bottom of the cooling structure assembly 1100, a coolant 902, a seal 904, an internal seal 1106 and a liquid inlet/outlet pair 1102 and 1104. The cooling structure assembly 1100 of FIG. 11 is similar to the cooling structure assembly 900 of FIG. 9 except for the presence of the internal seal 1106 and the liquid inlet/outlet pair 1102 and 1104. The cooling structure 1100 can also include a pair of flow-restricting end-plates (not shown in this figure but described in greater detail below).

The internal seal 1106 provides a seal within the space filling the areas created by the gap created between the microprocessor 102 and the top layer 106. The internal seal 1106 is located at a point in the cooling structure assembly 1100 where the fin structures 702 of the array of spring elements 710 end. That is, the height of the internal seal 1106 is the height at which the fin structure 702 ends and the spring portion begins, for each of the array of spring elements 710. This is the ideal location for the internal seal 1106, as it forces the coolant 902 to travel within the area of the fin structures 702 of the array of spring elements 710, which is where a higher degree of heat dissipation occurs in the cooling structure assembly 1100.

FIG. 11 also shows an inlet/outlet pair 1102 and 1104. The inlet 1102 allows for the intake of the coolant 902 as it is pumped or otherwise pushed or propelled into the assembly 1100. As the coolant 902 travels in the space filling the areas created by the gap created between the microprocessor 102 and the top layer 106 (namely, the area of the fin structures 702 of the array of spring elements 710), the coolant 902 absorbs the heat emanated from the first layer 104 and the fin structures 702 of the array of spring elements 710. The outlet 1104 allows for the egress of the coolant 902 as it is pumped or otherwise pulled or propelled out of the assembly 1100 for cooling and eventual recycling into the assembly 1100.

Figure 12:
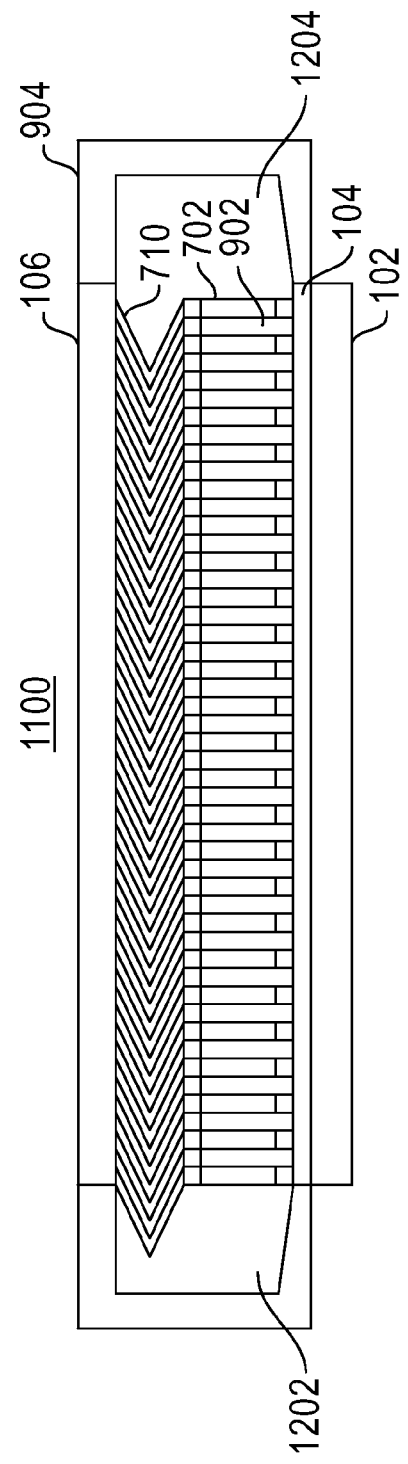
FIG. 12 is another cross-sectional side view of the cooling structure of FIG. 11.

FIG. 12 is another cross-sectional side view of the cooling structure of FIG. 11. FIG. 12 shows the cooling structure assembly 1100 comprising the top layer 106, the first layer 104 and the array of spring elements 710 disposed between them. FIG. 12 also shows the microprocessor 102 at the bottom of the cooling structure assembly 1100, a thermal interface material 902, a seal 904 and an internal seal 1106. The cooling structure 1100 can also include a pair of flow-restricting end-plates 1202 and 1204 that fill the area on either end of the array of spring elements 710 in FIG. 12. The purpose of the end-plates 1202 and 1204 is to restrict the flow of the coolant 902 into those spaces so as to force the coolant 902 to flow in the area between the multiple spring elements, which is where a higher degree of heat dissipation occurs.

Figure 13:
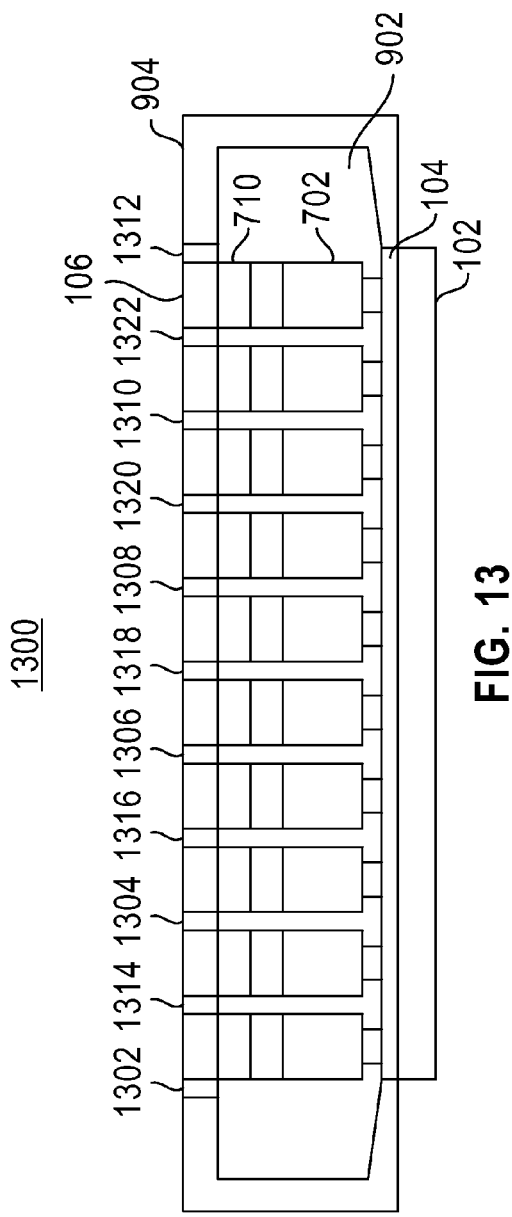
FIG. 13 is a cross-sectional side view of a cooling structure for an electronic device, the cooling structure including spring elements with a fin, a plate, liquid inlets/outlets and a liquid, according to one embodiment of the present invention.

FIG. 13 is a cross-sectional side view of a cooling structure for an electronic device, the cooling structure including spring elements with a fin, a plate, inlets/outlets and a coolant, according to one embodiment of the present invention. FIG. 13 shows the cooling structure assembly 1300 comprising the top layer 106, the first layer 104 and the array of spring elements 710 disposed between them. FIG. 13 also shows the microprocessor 102 at the bottom of the cooling structure assembly 1100, a coolant 902, a seal 904 and a series of inlets/outlets. The cooling structure assembly 1300 of FIG. 13 is similar to the cooling structure assembly 1100 of FIG. 11 except for the presence of the series of inlets/outlets and the lack of the internal seal 1106. The cooling structure 1300 can also include a pair of flow-restricting end-plates (not shown in this figure but described in greater detail below).

FIG. 13 also shows a series of inlets/outlets. Orifices 1302, 1304, 1306, 1308, 1310 and 1312 are designated as inlets. Orifices 1314, 1316, 1318, 1320 and 1322 are designated as outlets. The inlets allow for the intake of the coolant 902 as it is pumped or otherwise pushed or propelled into the assembly 1300. As the coolant 902 travels in the space filling the areas created by the gap created between the microprocessor 102 and the top layer 106 (namely, the area of the array of spring elements 710), the coolant 902 absorbs the heat emanated from the first layer 104 and the array of spring elements 710. The outlets allow for the egress of the coolant 902 as it is pumped or otherwise pulled or propelled out of the assembly 1300 for cooling and eventual recycling into the assembly 1300.

Figure 14:
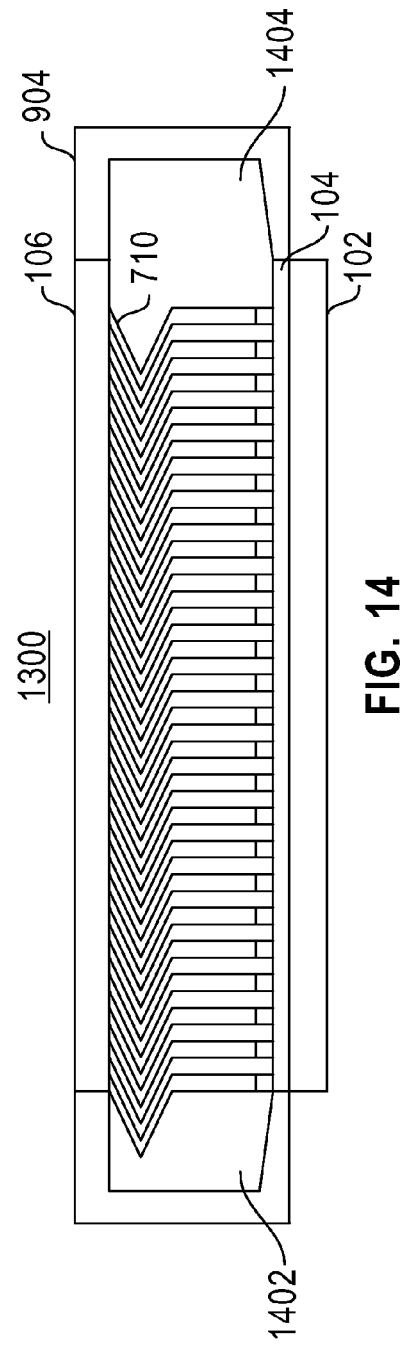
FIG. 14 is another cross-sectional side view of the cooling structure of FIG. 13.

FIG. 14 is another cross-sectional side view of the cooling structure of FIG. 13. FIG. 14 shows the cooling structure assembly 1300 comprising the top layer 106, the first layer 104 and the array of spring elements 710 disposed between them. FIG. 14 also shows the microprocessor 102 at the bottom of the cooling structure assembly 1300, a coolant 902 and a seal 904. The cooling structure 1300 can also include a pair of flow-restricting end-plates 1402 and 1404 that fill the area on either end of the array of spring elements 710 in FIG. 14.

Figure 15:
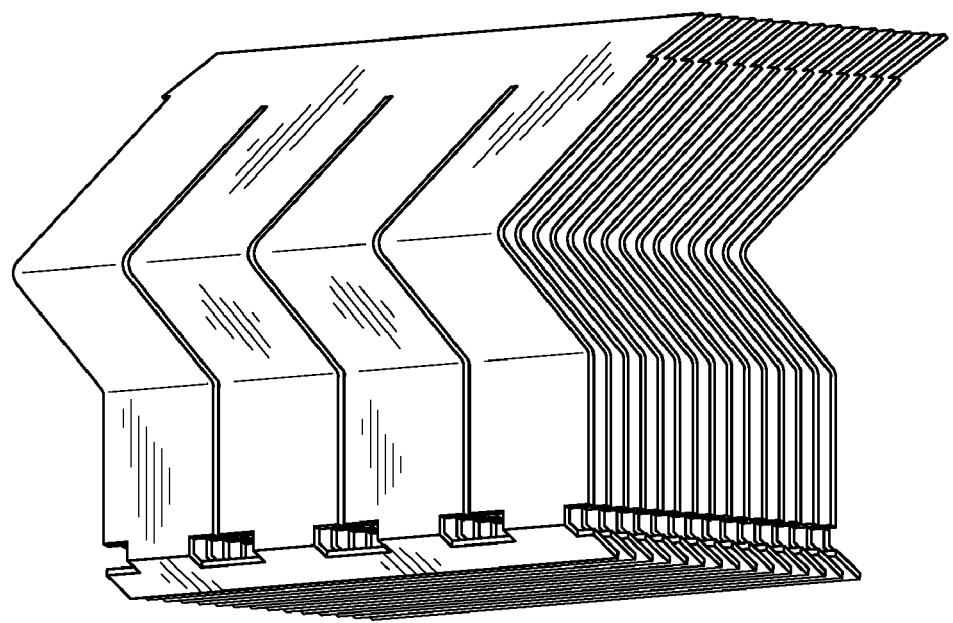
FIG. 15 is a perspective view of a series of spring elements in a stacked arrangement.

FIG. 15 is a perspective view of a series of spring elements in a stacked arrangement. A uniform first distance exists between each spring element. Note each of the spring elements comprises a single sheet of material, such as a thermally conductive sheet of metal such as copper, that includes sections that are drilled out or removed. The spring elements of FIG. 15 are examples of spring elements that can be used in any of the cooling structure assemblies 100, 300, 500, 700, 900, 1100 and 1300. The stacked nature of the spring elements of FIG. 15 show how the spring elements can be arranged for inclusion into any of the aforementioned cooling structure assemblies. Note that FIGS. 15-17 show the series of spring elements as they are stacked during assembly of a microprocessor assembly that includes the present invention, in one embodiment.

Figure 16:
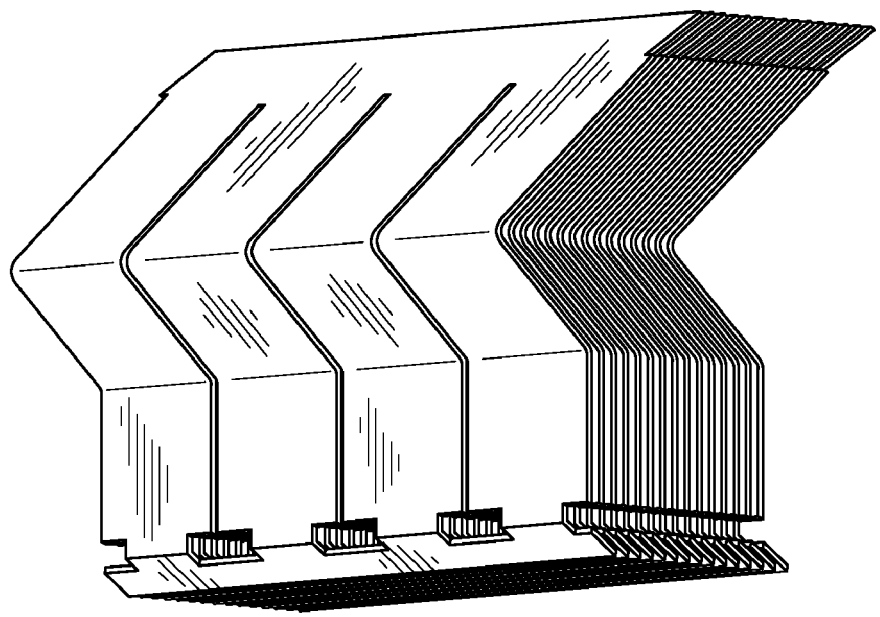
FIG. 16 shows the spring elements of FIG. 15 in a tighter stacked arrangement.
Figure 17:
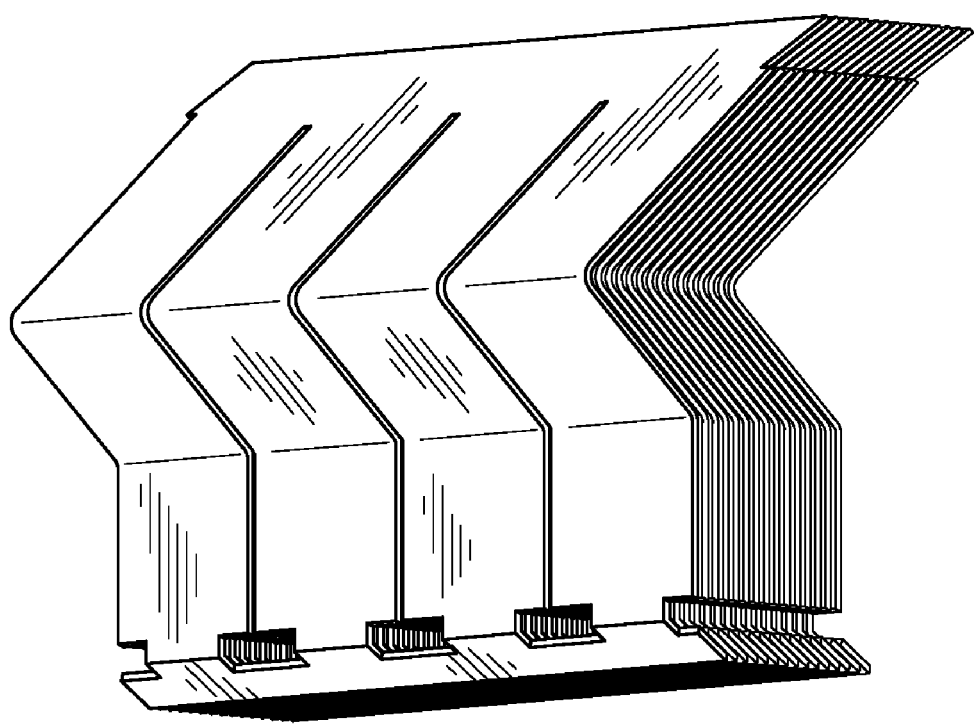
FIG. 17 shows the spring elements of FIG. 15 in an even tighter stacked arrangement.

FIG. 16 shows the spring elements of FIG. 15 in a tighter stacked arrangement. A uniform second distance exists between each spring element, wherein the second distance is shorter than the first distance. FIG. 17 shows the spring elements of FIG. 15 in an even tighter stacked arrangement. A uniform third distance exists between each spring element, wherein the third distance is shorter than the second distance.

Figure 18:
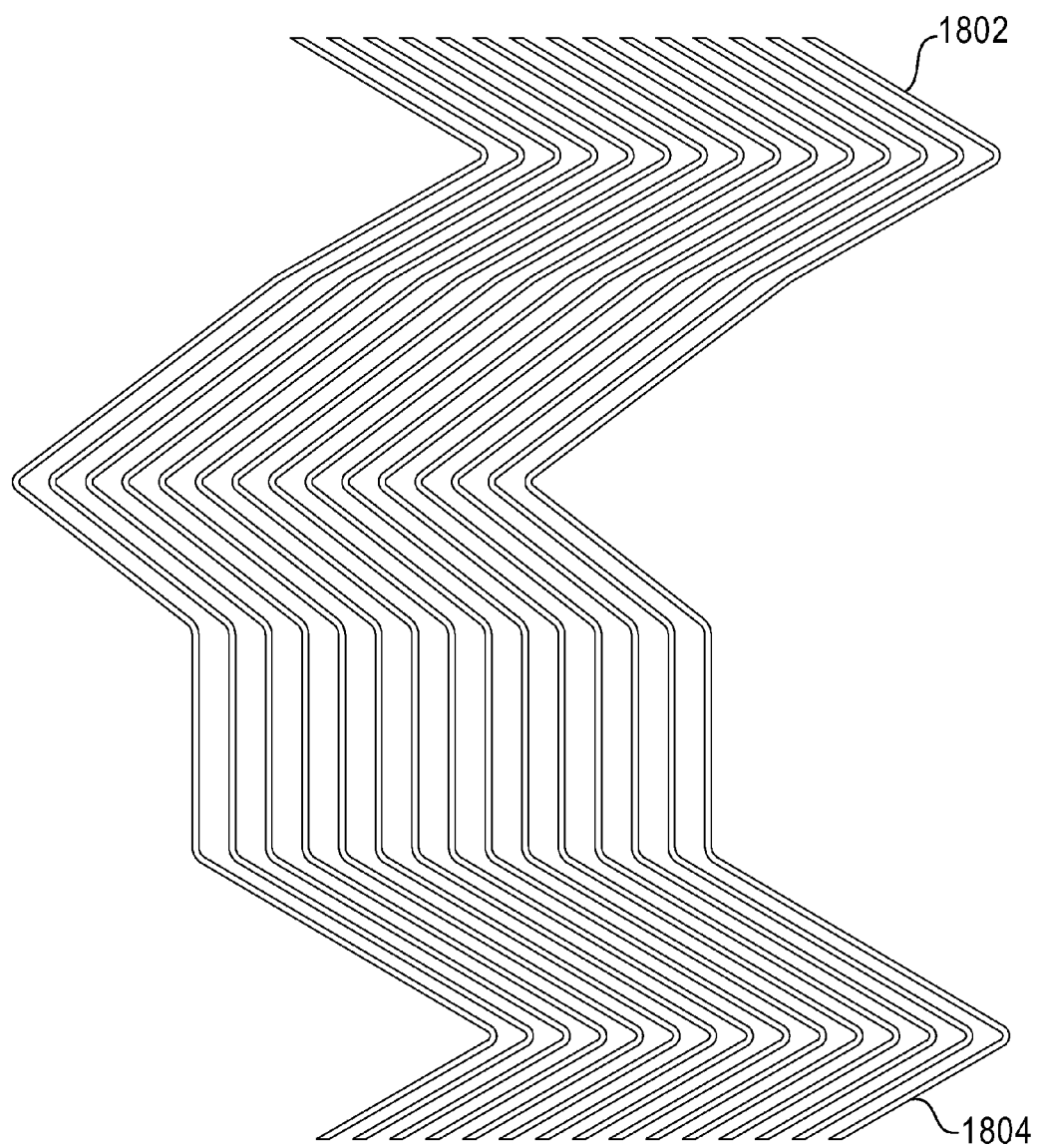
FIG. 18 is a cross-sectional side view of spring elements in a stacked arrangement.

FIG. 18 is a cross-sectional side view of spring elements in a stacked arrangement. A uniform first distance exists between each spring element. Compared to the spring elements of FIG. 15, note that the spring elements of FIG. 18 each include an additional element 1802 on the top end of the spring elements and an additional element 1804 on the bottom end of the spring elements. Note that FIGS. 18-20 show the series of spring elements as they are stacked during assembly of a microprocessor assembly that includes the present invention, in one embodiment.

Figure 19:
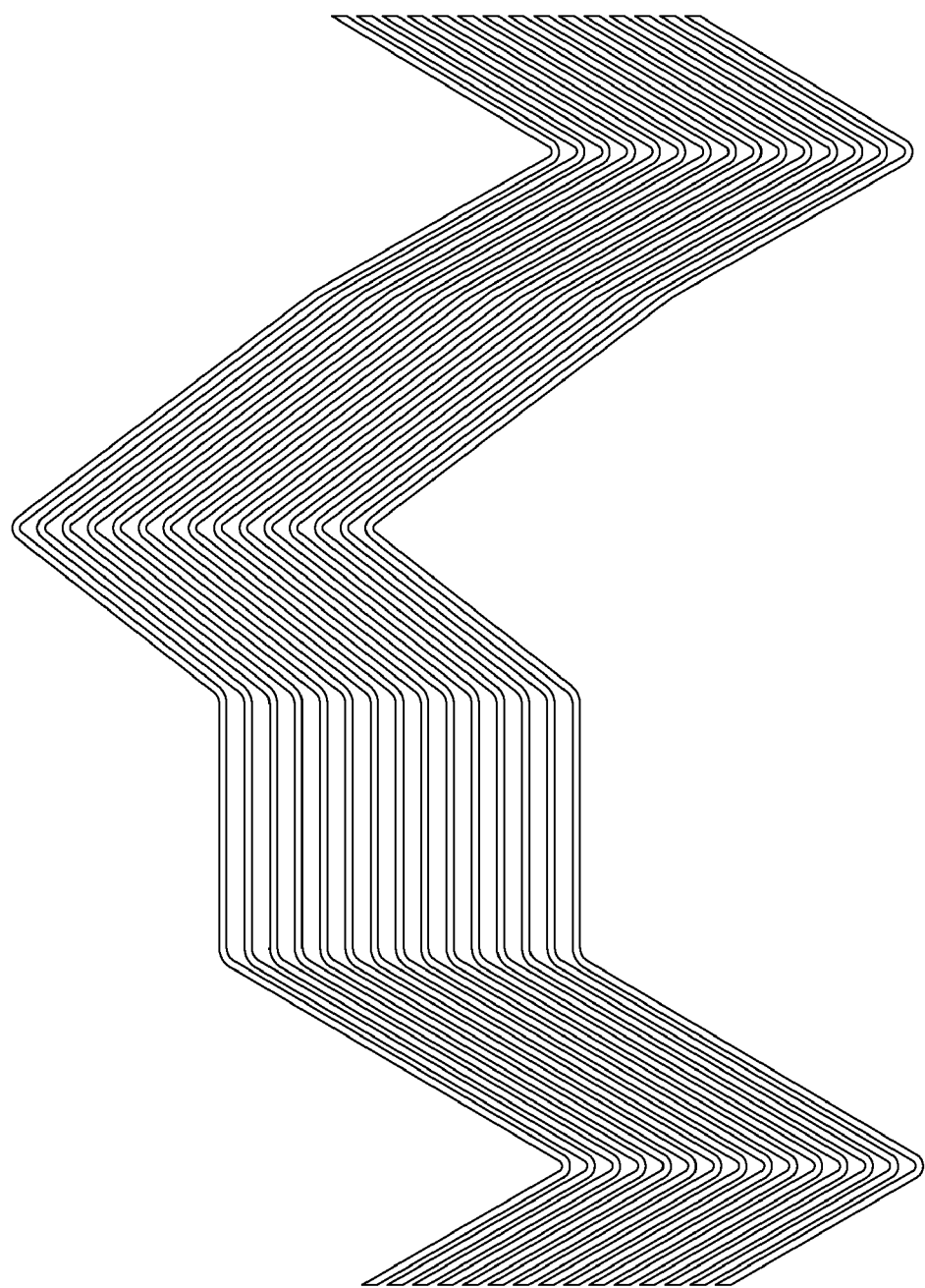
FIG. 19 shows the spring elements of FIG. 18 in a tighter stacked arrangement.
Figure 20:
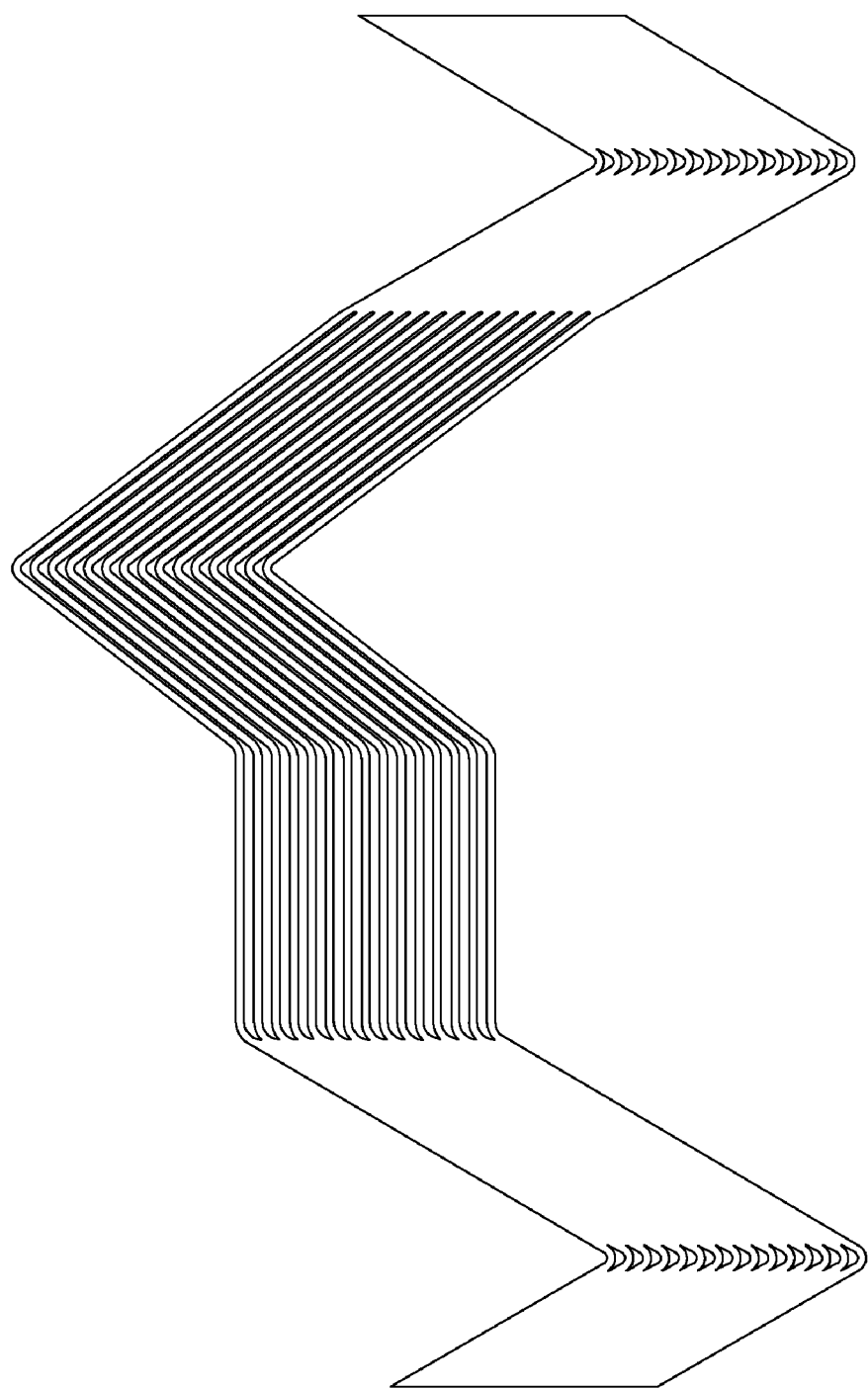
FIG. 20 shows the spring elements of FIG. 18 in an even tighter stacked arrangement.
Figure 21:
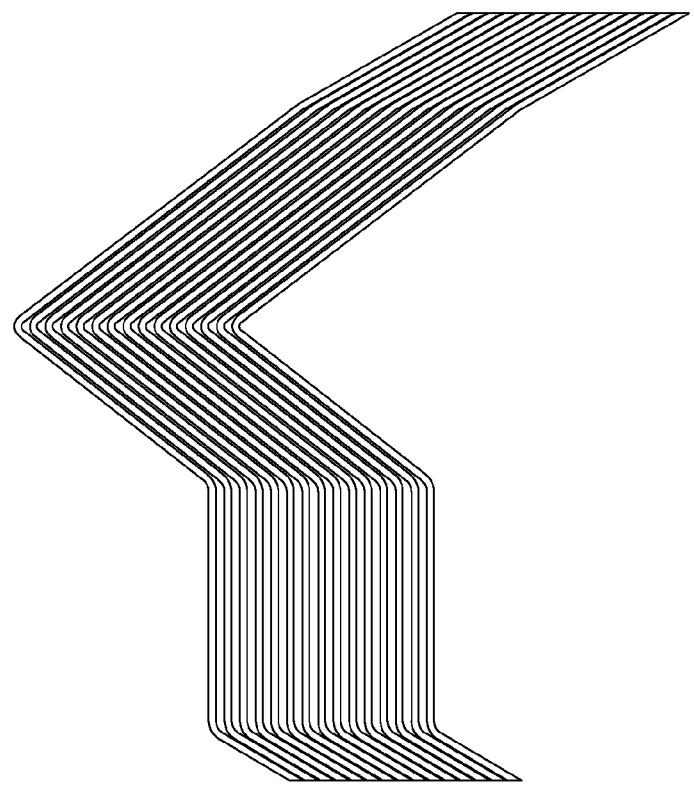
FIG. 21 shows the spring elements of FIG. 18 in an even tighter stacked arrangement.

FIG. 19 shows the spring elements of FIG. 18 in a tighter stacked arrangement. A uniform second distance exists between each spring element, wherein the second distance is shorter than the first distance. FIG. 20 shows the spring elements of FIG. 18 in an even tighter stacked arrangement. A uniform third distance exists between each spring element, wherein the third distance is shorter than the second distance. FIG. 21 shows the spring elements of FIG. 18 in an even tighter stacked arrangement. A uniform fourth distance exists between each spring element, wherein the fourth distance is shorter than the third distance. Note in FIG. 21 that the additional element 1802 on the top end of the spring elements and the additional element 1804 on the bottom end of the spring elements has been removed. That is, the spring elements have been trimmed.

Figure 22:
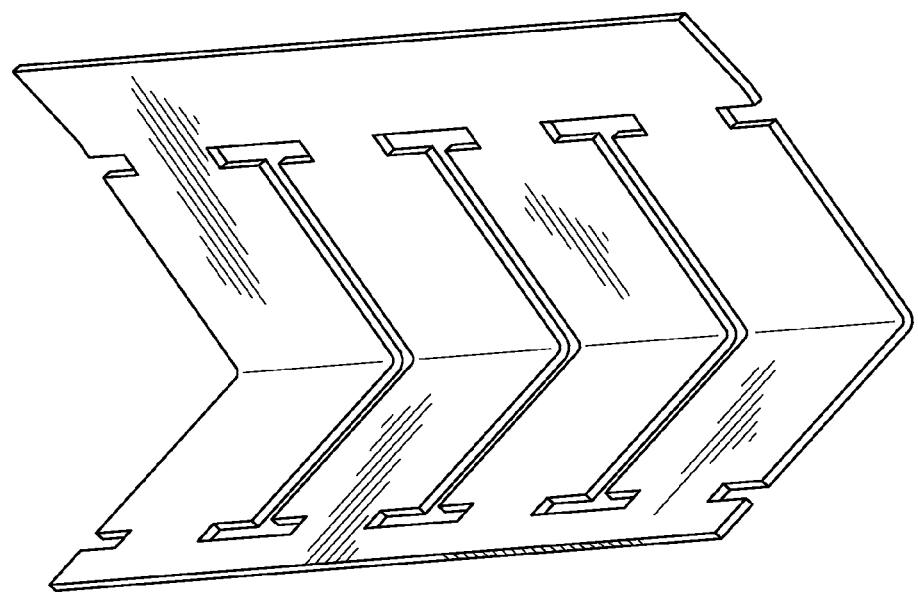
FIG. 22 is a perspective view of a spring element.
Figure 23:
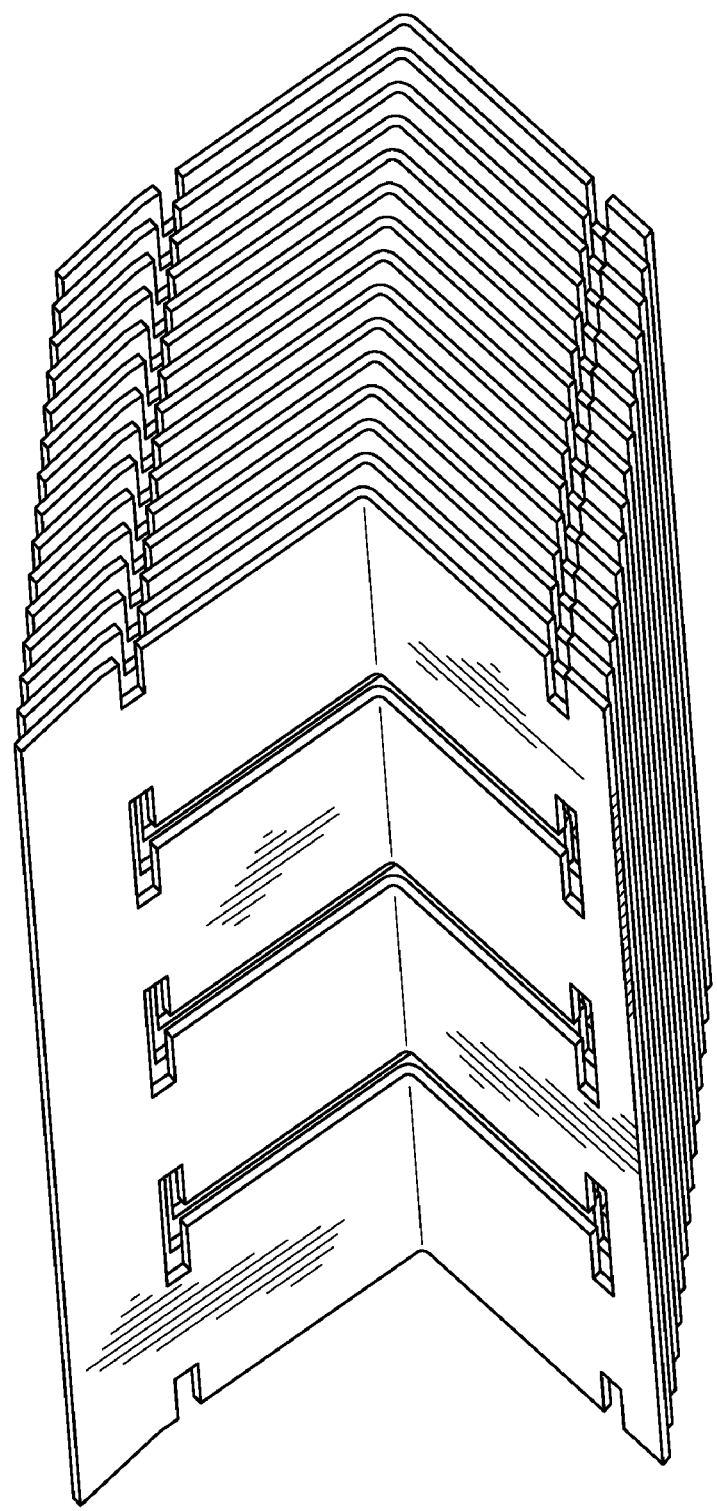
FIG. 23 is a perspective view of a series of spring elements of FIG. 22 in a stacked arrangement.

FIG. 22 is a perspective view of a spring element. Note that the spring element comprises a single sheet of material, such as a thermally conductive sheet of metal such as copper, that includes sections that are drilled out or removed. The spring element of FIG. 15 is an example of a spring element that can be used in any of the cooling structure assemblies 100, 300, 500, 700, 900, 1100 and 1300. FIG. 23 is a perspective view of a series of spring elements of FIG. 22 in a stacked arrangement. A uniform first distance exists between each spring element. The stacked nature of the spring elements of FIG. 23 show how the spring elements can be arranged for inclusion into any of the aforementioned cooling structure assemblies.

Figure 24:
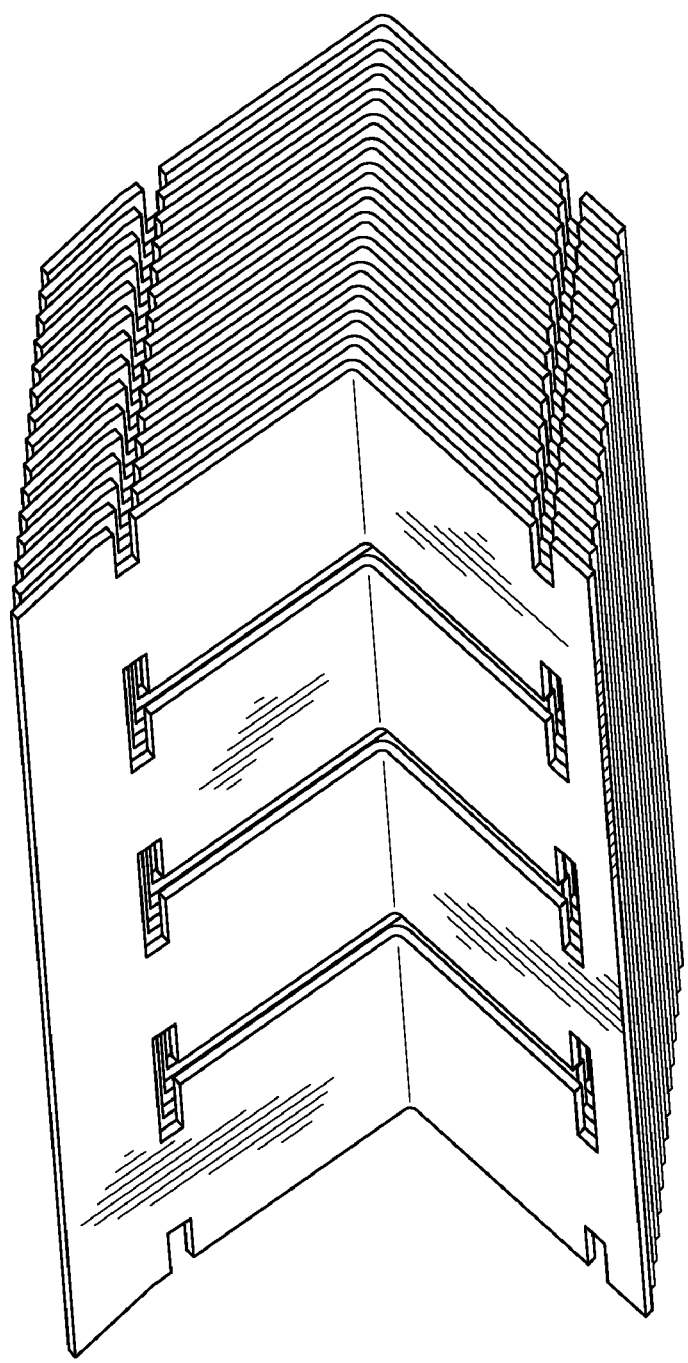
FIG. 24 shows the spring elements of FIG. 23 in a tighter stacked arrangement.
Figure 25:
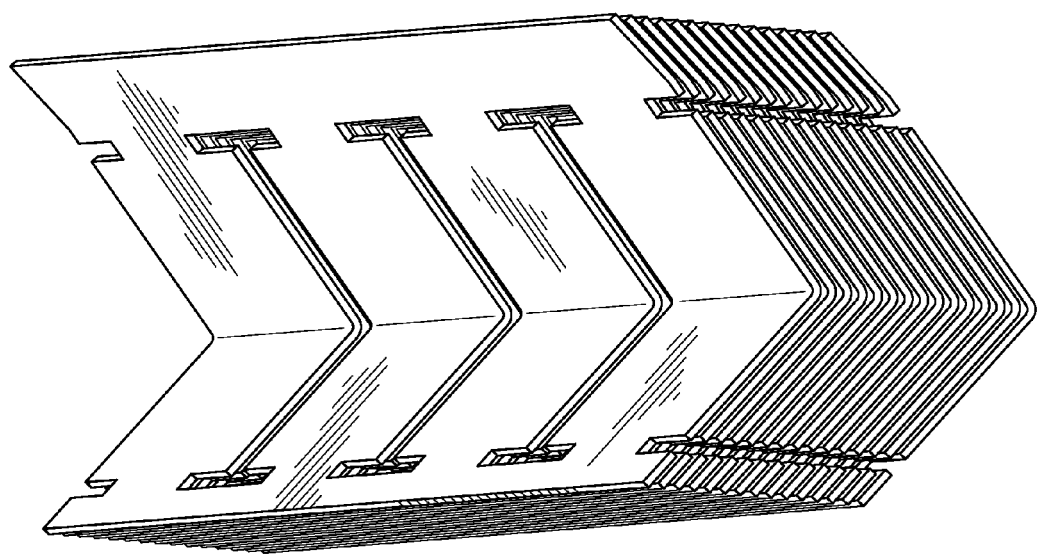
FIG. 25 shows the spring elements of FIG. 23 in an even tighter stacked arrangement.

FIG. 24 shows the spring elements of FIG. 23 in a tighter stacked arrangement. A uniform second distance exists between each spring element, wherein the second distance is shorter than the first distance. FIG. 25 shows the spring elements of FIG. 23 in an even tighter stacked arrangement. A uniform third distance exists between each spring element, wherein the third distance is shorter than the second distance.

Figure 26:
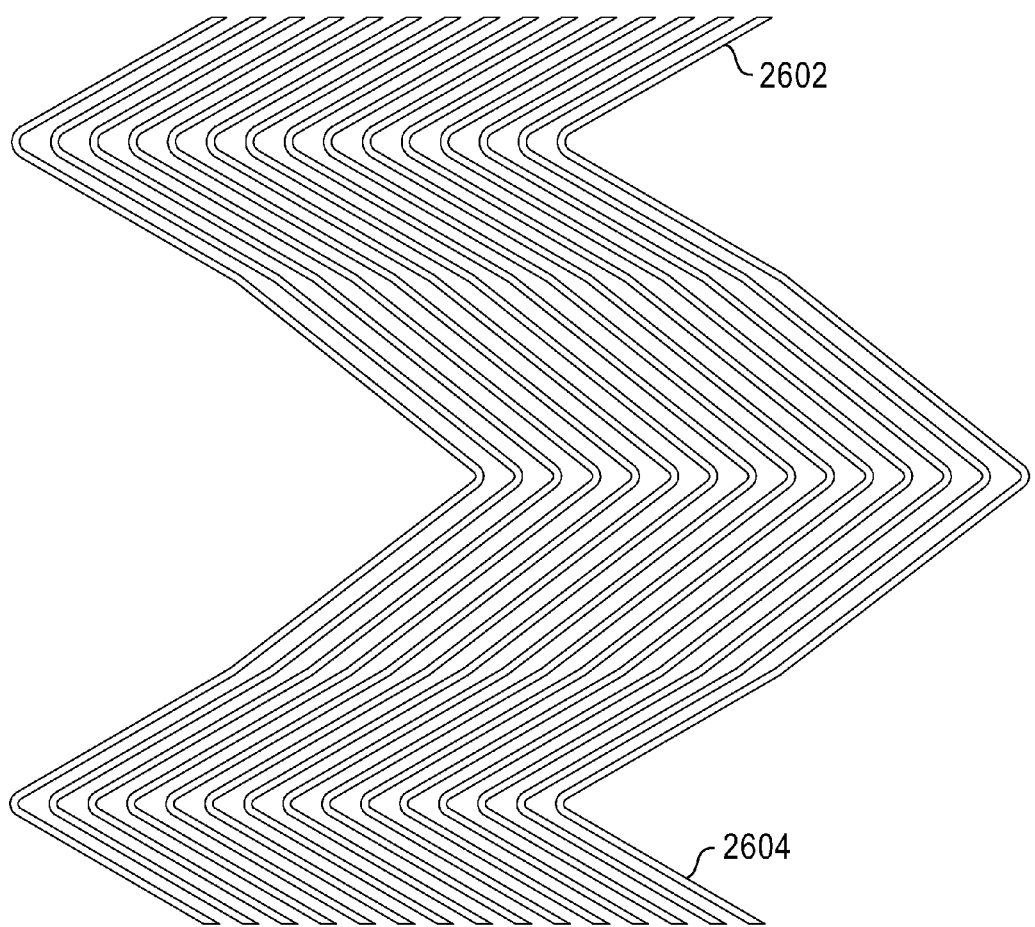
FIG. 26 is a cross-sectional side view of spring elements in a stacked arrangement.
Figure 27:
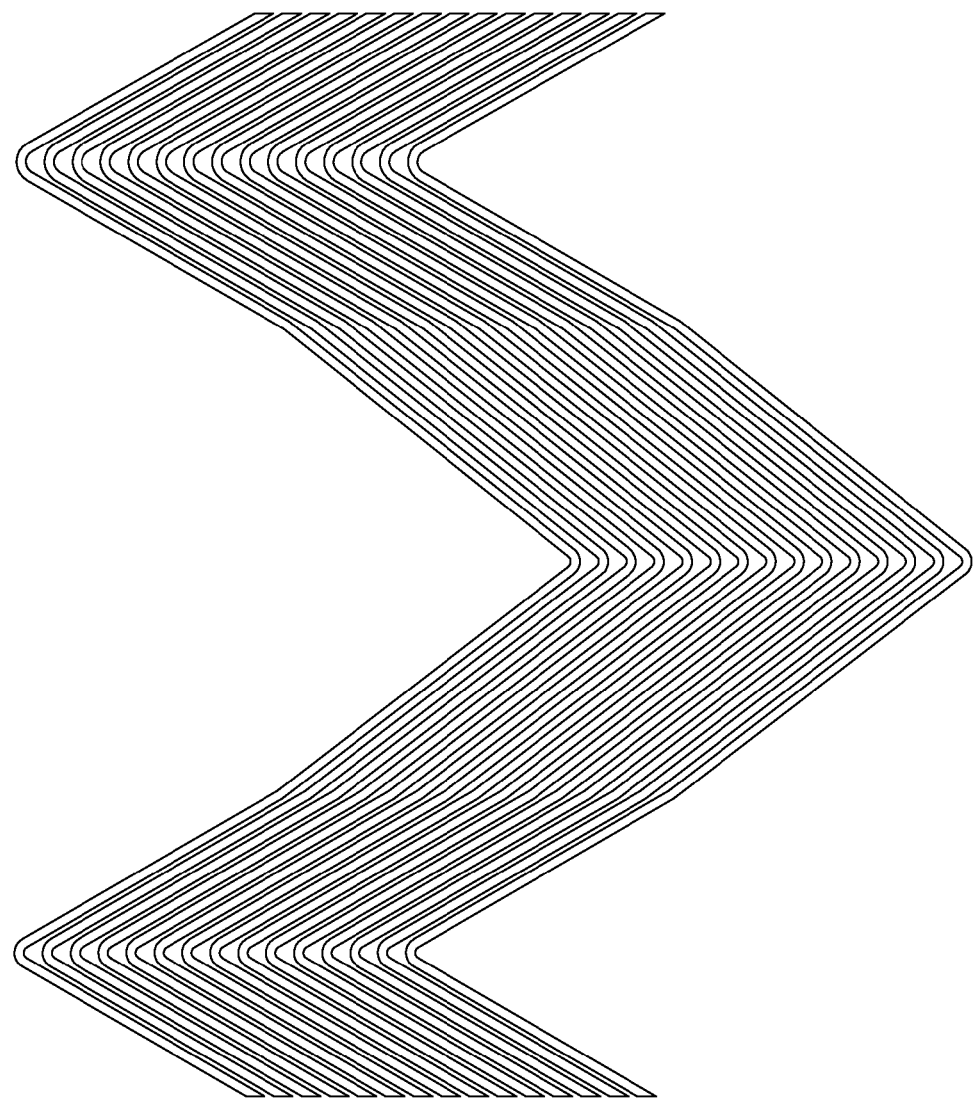
FIG. 27 shows the spring elements of FIG. 26 in a tighter stacked arrangement.
Figure 28:
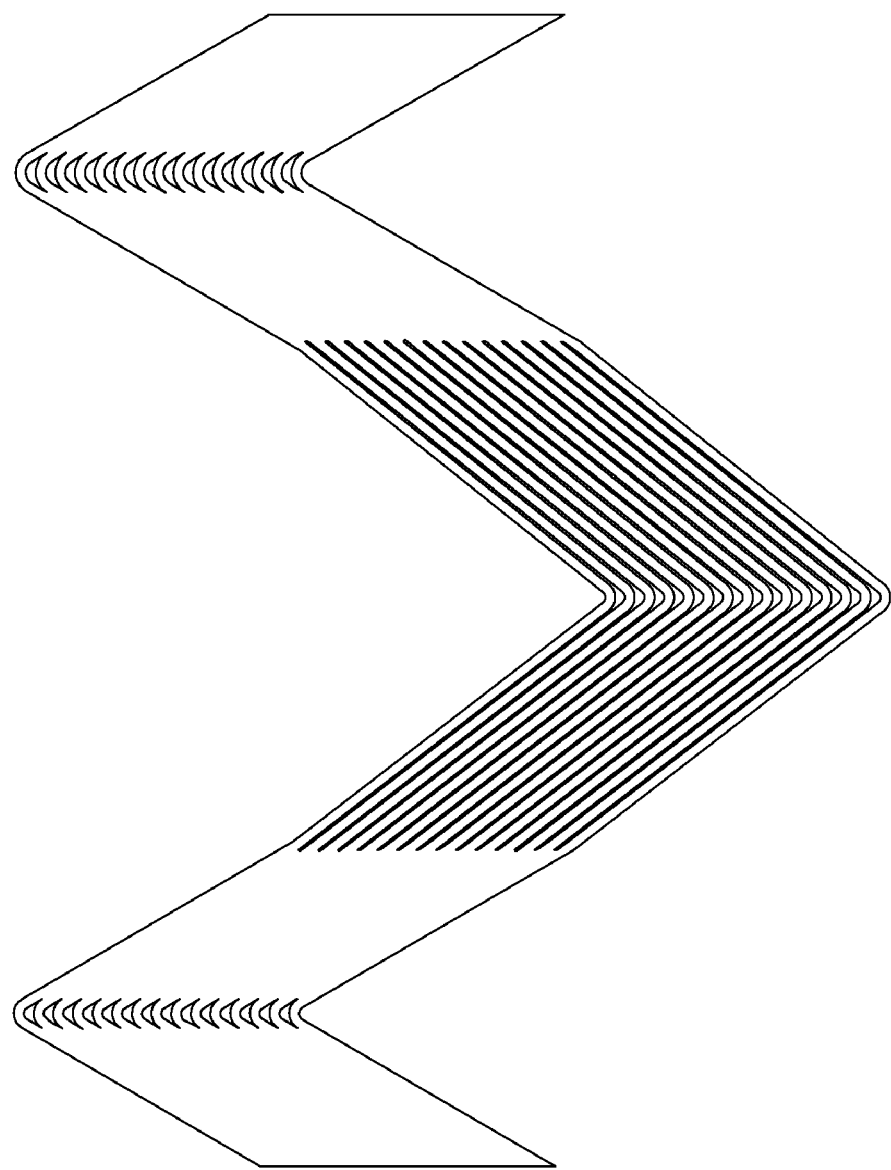
FIG. 28 shows the spring elements of FIG. 26 in an even tighter stacked arrangement.
Figure 29:
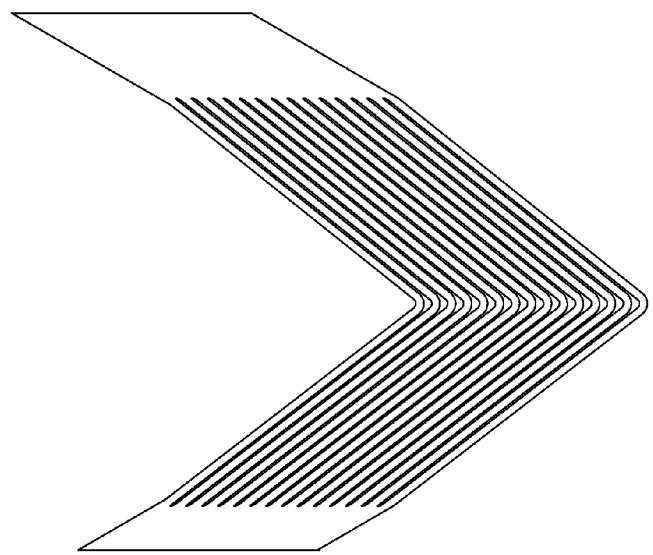
FIG. 29 shows the spring elements of FIG. 26 in an even tighter stacked arrangement.

FIG. 26 is a cross-sectional side view of spring elements in a stacked arrangement. A uniform first distance exists between each spring element. Compared to the spring elements of FIG. 23, note that the spring elements of FIG. 26 each include an additional element 2602 on the top end of the spring elements and an additional element 2604 on the bottom end of the spring elements. FIG. 27 shows the spring elements of FIG. 26 in a tighter stacked arrangement. A uniform second distance exists between each spring element, wherein the second distance is shorter than the first distance. FIG. 28 shows the spring elements of FIG. 26 in an even tighter stacked arrangement. A uniform third distance exists between each spring element, wherein the third distance is shorter than the second distance. FIG. 29 shows the spring elements of FIG. 26 in an even tighter stacked arrangement. A uniform fourth distance exists between each spring element, wherein the fourth distance is shorter than the third distance. Note in FIG. 29 that the additional element 2602 on the top end of the spring elements and the additional element 2604 on the bottom end of the spring elements has been removed.

Figure 30:
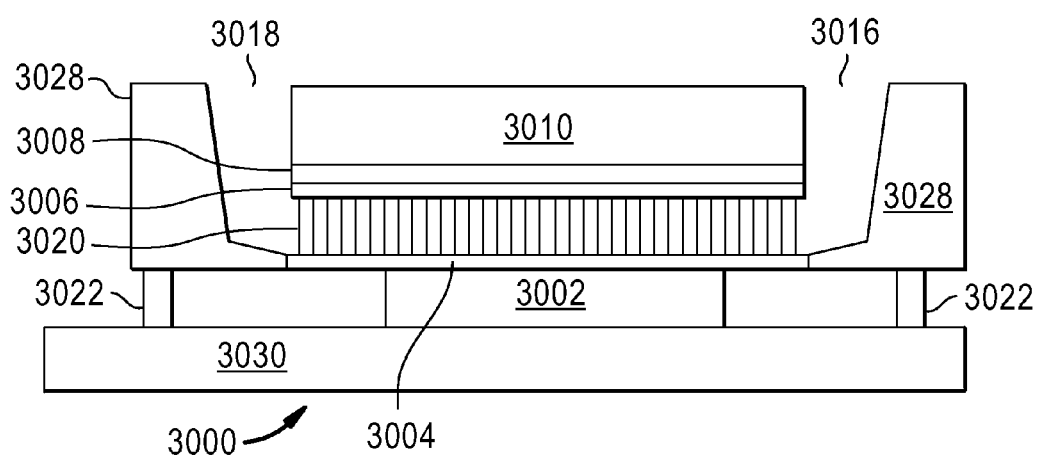
FIG. 30 is a cross-sectional side view of a cooling structure for an electronic device, the cooling structure including rod elements and a liquid coolant, according to one embodiment of the present invention.

FIG. 30 is a cross-sectional side view of a cooling structure for an electronic device, the cooling structure including rod elements and a liquid coolant, according to one embodiment of the present invention. FIG. 30 shows a heat-producing electronic device, a microprocessor 3002, located along the bottom of the assembly 3000. The microprocessor 3002 is disposed, such as through welding or soldering, onto a circuit board 3030. An attachment 3022 surrounds the microprocessor 3002 and provides a base for placing the rigid structure 3028 such that it is located above or over the microprocessor 3002. The structure 3010 is also a rigid structure that may be integrated with or separate from the rigid structure 3028.

Disposed on the microprocessor 3002 is a first layer 3004, which is a conformable high thermo conductivity membrane for providing a heat path from the microprocessor 3002 to the upper elements of the assembly 3000. The first layer 3004 is a planar surface that rests in contact with the microprocessor 3002. Disposed above the first layer 3004 is a second 3006, which can also be a conformable high thermo conductivity membrane for providing a heat path from the microprocessor 3002 to the upper elements of the assembly 3000. The second layer 3006 is a planar surface that rests in contact with a compressible material layer 3008, such as rubber. The layer 3006 is used as an adhesion/water-seal layer that is soft or pliable.

The term membrane refers to a thin substrate used to separate different layers or materials. There is no inherent application of tension assumed in conjunction with use of this term. The membranes described above can be foils or flexible sheets.

The cooling structure assembly 3000 further includes an array of rigid rod elements 3020 that contact or are coupled with the first layer 3004 and the second layer 3006. The array of rigid rod elements 3020 are disposed between the first layer 3004 and the second layer 3006. The array of rod elements 3020 comprise a plurality of rods or small cylinders extending in the upper direction away from the source of the heat, the microprocessor 3002. Each of the array of rod elements 3020 draw heat away from the microprocessor 3002 and allows the heat to radiate out from the increased surface area of the rod elements 3020. Each of the array of rod elements 3020 is comprised of a semi-rigid, high thermal conductivity material, such as copper. Further, the array of rod elements 3020 are packed densely.

Due to the conformable nature of the first layer 3004 and the second layer 3006, each individual rod element has the freedom to move upwards or downwards. Further, due to the compressible nature of the compressible material layer 3008, each individual rod element has the freedom to move upwards into the compressible material layer 3008 or downwards away from compressible material layer 3008, as the dimensions of the microprocessor 3002 change due to heat buildup during use. Thus, the compressible material layer 3008 allows for compression and elongation in the z-direction, i.e., the up and down direction, and in the x, y-directions, i.e., the sideways directions. This provides heat compliance in accordance with dimensional changes in the microprocessor 102 during use.

FIG. 30 also shows a thermal interface material 3024 located in the gap created between the structure 3010 and the structure 3028 and in the area between first layer 3004 and the second layer 3006. The thermal interface material 3024 can be a non-metal liquid thermal interface material, such as oil or water, or a metal liquid thermal interface material such as mercury, gallium or a gallium alloy such as with tin or indium. The thermal interface material 3024 can be sealed so as to restrict the escape of the thermal interface material 3024 from the desired area over the microprocessor 3002. The liquid nature of the thermal interface material 3024 allows the substance to fill the areas created by the gap created between the structure 3010 and the structure 3028 and in the area between first layer 3004 and the second layer 3006. The thermal interface material 3024 provides a heat path from the microprocessor 3002 to the upper elements of the assembly 3000 as the heat travels from the microprocessor 3002 upwards.

FIG. 30 also shows a liquid inlet/outlet pair 3016 and 3018. The liquid inlet 3016 allows for the intake of the liquid thermal interface material 3024 as it is pumped or otherwise pushed or propelled into the assembly 3000. As the liquid thermal interface material 3024 travels in the space filling the areas created by the gap created between the structure 3010 and the structure 3028 and in the area between first layer 3004 and the second layer 3006, the liquid thermal interface material 3024 absorbs the heat emanated from the first layer 3004 and the array of rod elements 3020. The liquid outlet 3018 allows for the egress of the liquid thermal interface material 3024 as it is pumped or otherwise pulled or propelled out of the assembly 3000 for cooling and eventual recycling into the assembly 3000.

Figure 31:
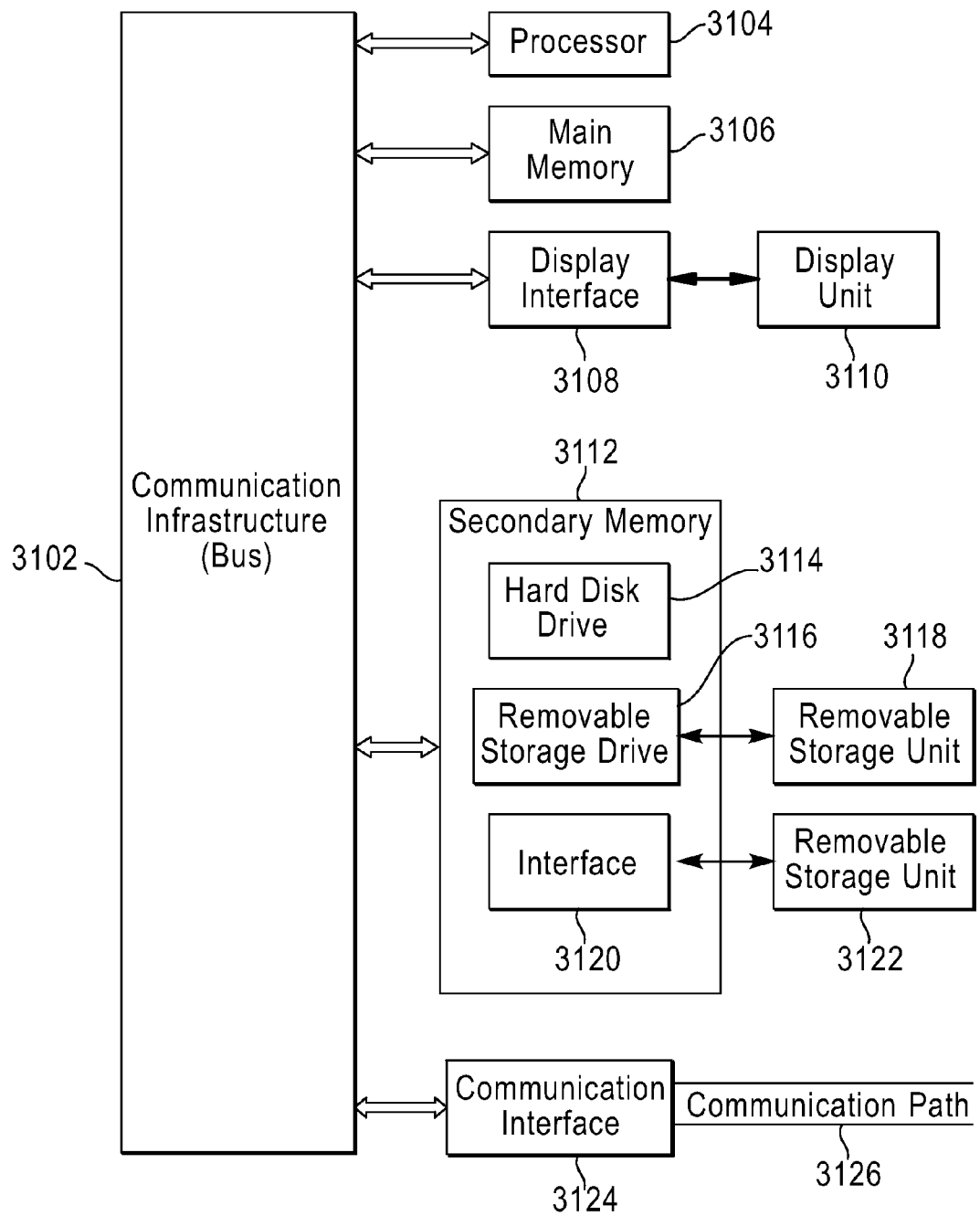
FIG. 31 is a high level block diagram showing an information processing system useful for implementing one embodiment of the present invention.
Figure 32:
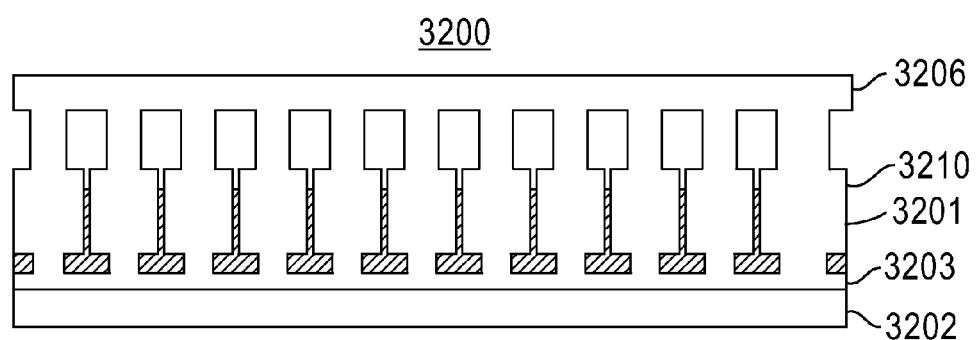
FIG. 32 is a cross-sectional side view of a cooling structure for an electronic device, the cooling structure includes a liquid with vaporizing capability, a compliant membrane and spring elements with fins, according to one embodiment of the present invention.
Figure 33:
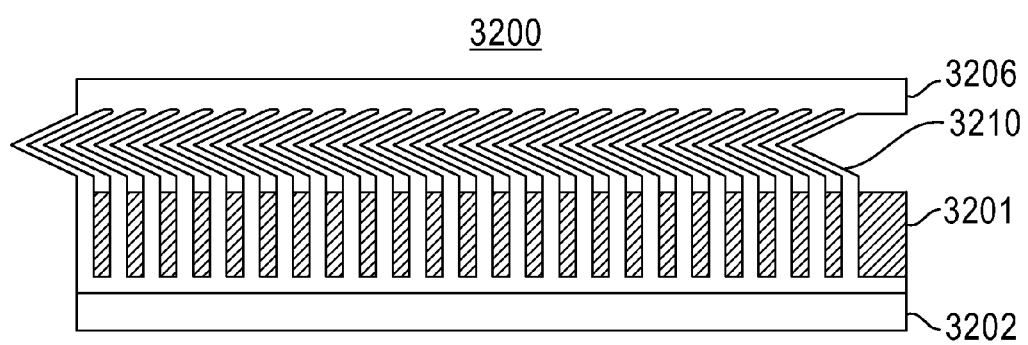
FIG. 33 is another cross-sectional side view of the cooling structure of FIG. 32.
Figure 34:
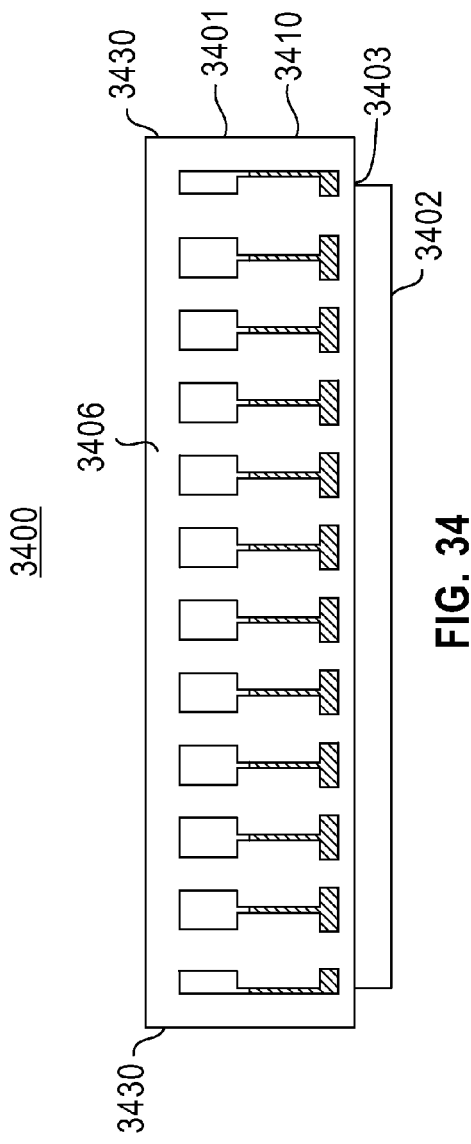
FIG. 34 is a cross-sectional side view of a cooling structure for an electronic device, the cooling structure includes a container for containing a liquid with vaporizing capability, a compliant membrane and spring elements with fins, according to one embodiment of the present invention.
Figure 35:
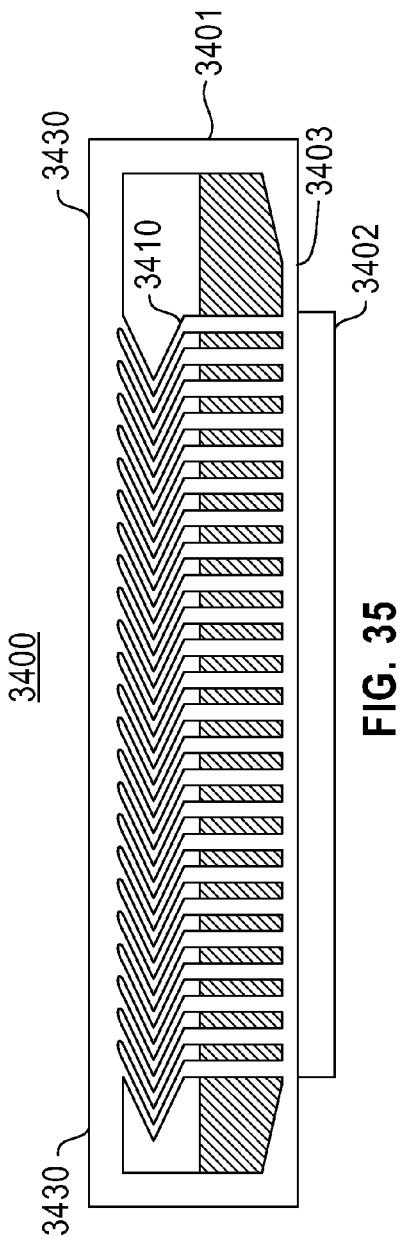
FIG. 35 is another cross-sectional side view of the cooling structure of FIG. 34.
Figure 36:
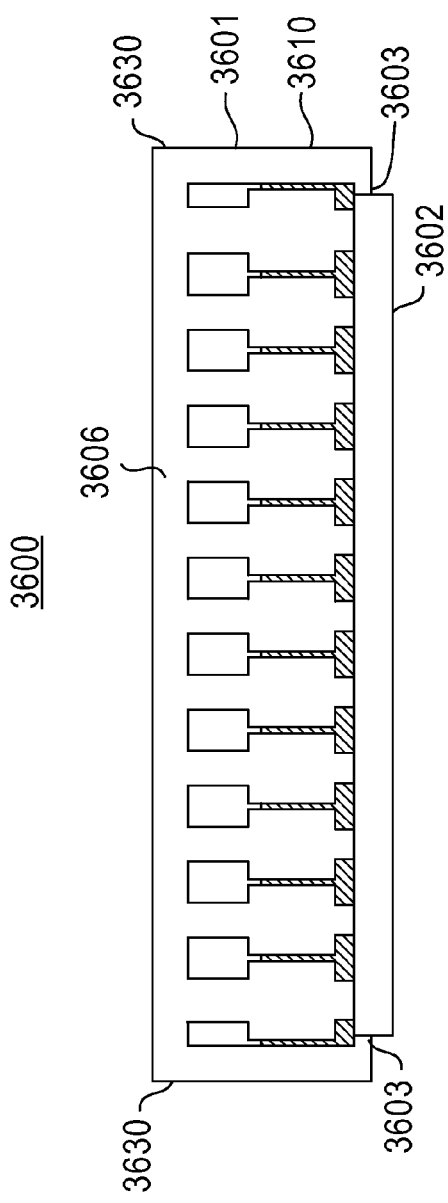
FIG. 36 is a cross-sectional side view of a cooling structure for an electronic device, the cooling structure includes a container for containing a liquid with vaporizing capability and spring elements with fins, according to one embodiment of the present invention.
Figure 37:
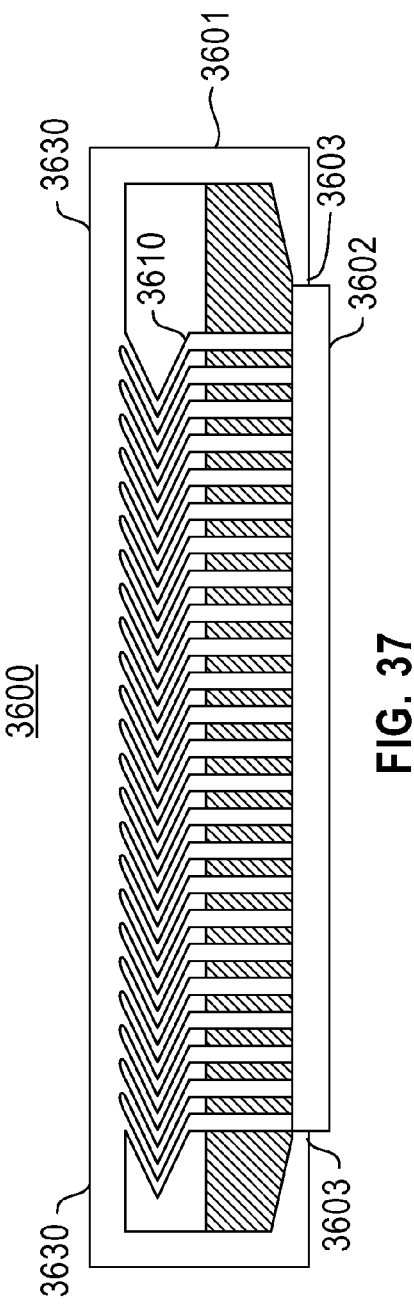
FIG. 37 is another cross-sectional side view of the cooling structure of FIG. 36.
Figure 38:
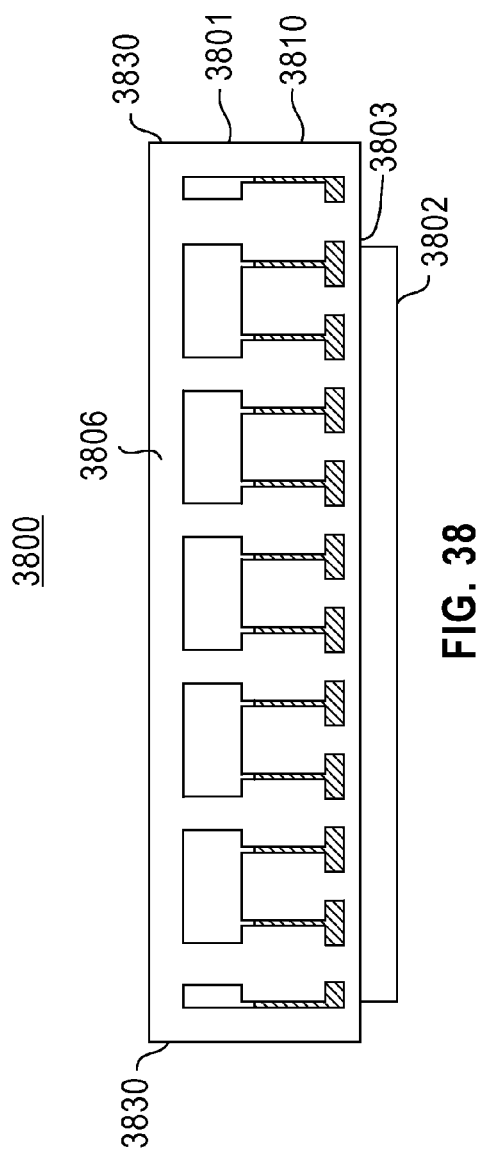
FIG. 38 is a cross-sectional side view of a cooling structure for an electronic device, the cooling structure includes a container for containing a liquid with vaporizing capability, a compliant membrane and alternating spring elements with fins, according to one embodiment of the present invention.
Figure 39:
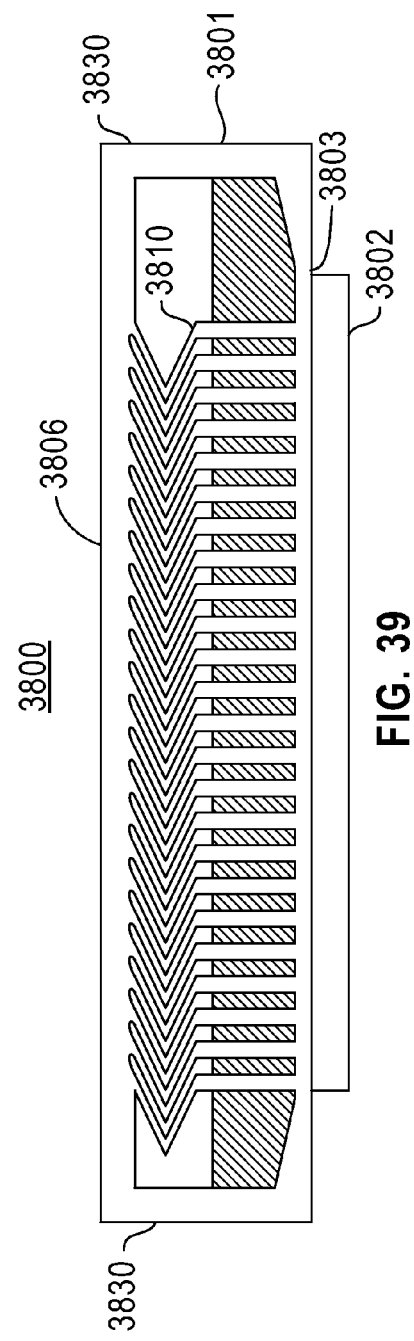
FIG. 39 is another cross-sectional side view of the cooling structure of FIG. 38.

The present invention can be utilized for cooling any of a variety of electronic devices. In one embodiment of the present invention, the present invention is used to cool a microprocessor of an information processing system such as a computer. FIG. 31 is a high level block diagram showing an information processing system useful for implementing one embodiment of the present invention. The computer system includes one or more processors, such as processor 3104. The processor 3104 is connected to a communication infrastructure 3102 (e.g., a communications bus, cross-over bar, or network). Various software embodiments are described in terms of this exemplary computer system. After reading this description, it will become apparent to a person of ordinary skill in the relevant art(s) how to implement the invention using other computer systems and/or computer architectures.

The computer system can include a display interface 3108 that forwards graphics, text, and other data from the communication infrastructure 3102 (or from a frame buffer not shown) for display on the display unit 3110. The computer system also includes a main memory 3106, preferably random access memory (RAM), and may also include a secondary memory 3112. The secondary memory 3112 may include, for example, a hard disk drive 3114 and/or a removable storage drive 3116, representing a floppy disk drive, a magnetic tape drive, an optical disk drive, etc. The removable storage drive 3116 reads from and/or writes to a removable storage unit 3118 in a manner well known to those having ordinary skill in the art. Removable storage unit 3118, represents a floppy disk, a compact disc, magnetic tape, optical disk, etc. which is read by and written to by removable storage drive 3116. As will be appreciated, the removable storage unit 3118 includes a computer readable medium having stored therein computer software and/or data.

In alternative embodiments, the secondary memory 3112 may include other similar means for allowing computer programs or other instructions to be loaded into the computer system. Such means may include, for example, a removable storage unit 3122 and an interface 3120. Examples of such may include a program cartridge and cartridge interface (such as that found in video game devices), a removable memory chip (such as an EPROM, or PROM) and associated socket, and other removable storage units 3122 and interfaces 3120 which allow software and data to be transferred from the removable storage unit 3122 to the computer system.

The computer system may also include a communications interface 3124. Communications interface 3124 allows software and data to be transferred between the computer system and external devices. Examples of communications interface 3124 may include a modem, a network interface (such as an Ethernet card), a communications port, a PCM-CIA slot and card, etc. Software and data transferred via communications interface 3124 are in the form of signals which may be, for example, electronic, electromagnetic, optical, or other signals capable of being received by communications interface 3124. These signals are provided to communications interface 3124 via a communications path (i.e., channel) 3126. This channel 3126 carries signals and may be implemented using wire or cable, fiber optics, a phone line, a cellular phone link, an RF link, and/or other communications channels.

In this document, the terms "computer program medium," "computer usable medium," and "computer readable medium" are used to generally refer to media such as main memory 3106 and secondary memory 3112, removable storage drive 3116, a hard disk installed in hard disk drive 3114, and signals. These computer program products are means for providing software to the computer system. The computer readable medium allows the computer system to read data, instructions, messages or message packets, and other computer readable information from the computer readable medium. The computer readable medium, for example, may include non-volatile memory, such as a floppy disk, ROM, flash memory, disk drive memory, a CD-ROM, and other permanent storage. It is useful, for example, for transporting information, such as data and computer instructions, between computer systems. Furthermore, the computer readable medium may comprise computer readable information in a transitory state medium such as a network link and/or a network interface, including a wired network or a wireless network, that allow a computer to read such computer readable information.

Computer programs (also called computer control logic) are stored in main memory 3106 and/or secondary memory 3112. Computer programs may also be received via communications interface 3124. Such computer programs, when executed, enable the computer system to perform the features of the present invention as discussed herein. In particular, the computer programs, when executed, enable the processor 3104 to perform the features of the computer system. Accordingly, such computer programs represent controllers of the computer system.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments. Furthermore, it is intended that the appended claims cover any and all such applications, modifications, and embodiments within the scope of the present invention.

We claim:

1. A structure for cooling an electronic device, comprising:
    a top layer disposed over the electronic device; and
    a plurality of spring elements disposed between the top layer and the electronic device for providing a heat path from the electronic device and wherein the plurality of spring elements provide mechanical compliance;
    wherein at least one of said spring elements has at least one section with a smaller contact area that gradually increases in cross section to the full cross section of the spring element to prevent the end of the spring elements from adding unwanted rigidity to the structure for cooling with minimal thermal resistance.

2. The structure of claim 1, wherein one end of each of the plurality of spring elements is coupled to the electronic device.

3. The structure of claim 1, farther comprising: a heat-conducting layer disposed over the electronic device, wherein the plurality of spring elements are coupled to the heat-conducting layer.

4. The structure of claim 3, wherein the heat-conducting layer comprises
    one or more of: thermally conductive paste; thermally conductive adhesive; solder; indium; and a heat conducting metal.

5. The structure of claim 1, wherein each of the plurality of spring elements comprises
    one or more of a leaf spring and a helical spring composed of a heat conducting metal.

6. The structure of claim 5, wherein each of the plurality of spring elements comprises copper.

7. The structure of claim 1, wherein the structure comprises
    the electronic device and
    the electronic device comprises a microprocessor.

8. A structure for cooling an electronic device, comprising:

a rigid top layer disposed over the electronic device;

a plurality of spring elements disposed between the top layer and the electronic device for providing a heat path from the electronic device and wherein the plurality of spring elements provide mechanical compliance; and any one of a liquid and semi-solid thermal interface material disposed between the plurality of spring elements;

wherein at least one of said spring elements has at least one section having a smaller contact area that gradually increases in cross section to the full cross section of the spring element to prevent the end of the spring elements from adding unwanted rigidity to the structure for cooling with minimal thermal resistance.

9. The structure of claim 8, wherein the plurality of spring elements are coupled to the electronic device.

10. The structure of claim 8, further comprising:

a heat-conducting layer disposed over the electronic device, wherein the plurality of spring elements are coupled to the heat-conducting layer.

11. The structure of claim 10, wherein the heat-conducting layer is composed one or more of: a thermally conductive paste; a thermally conductive adhesive; solder; indium; and a heat conducting element.

12. The structure of claim 8, wherein each of the plurality of spring elements comprises any one of a leaf spring and a helical spring composed of a heat conducting metal.

13. The structure of claim 12, wherein each of the plurality of spring elements comprises copper.

14. The structure of claim 8, wherein the structure comprises the electronic device and the electronic device comprises a microprocessor.

15. The structure of claim 8, wherein the thermal interface material comprises a liquid heat-conducting material.

16. The structure of claim 15, wherein the thermal interface material is a liquid metal comprising one or more of: mercury; gallium; and a gallium alloy.

17. The structure of claim 15, wherein the thermal interface material is a non-metal liquid comprising one or more of: oil and water.

18. The structure of claim 8, further comprising a seal for containing the thermal interface material.

19. An information processing system comprising a processor;

a memory;

an input/output subsystem;

a bus coupled to the processor, memory; and input/output subsystem; and a cooling structure for cooling the processor, the cooling structure comprising:

a top layer disposed over the electronic device; and a plurality of spring elements disposed between the top layer and the electronic device for providing a heat path from the electronic device and wherein the plurality of spring elements provide mechanical compliance; wherein at least one of said spring elements has at least one section with a smaller contact area that gradually increases in cross section to the full cross section of the spring element to prevent the end of the spring elements from adding unwanted rigidity to the structure for cooling with minimal thermal resistance.

* * * * *